US005736373A

United States Patent [19]

Hamilton

[11] Patent Number: 5,736,373
[45] Date of Patent: Apr. 7, 1998

[54] THERMOSTABLE DNA POLYMERASE FROM BACILLUS PALLIDUS

[75] Inventor: Paul T. Hamilton, Cary, N.C.

[73] Assignee: Becton, Dickinson and Company, Franklin Lakes, N.J.

[21] Appl. No.: 717,515

[22] Filed: Sep. 23, 1996

[51] Int. Cl.$^6$ .............................. C12N 9/12; C12N 15/54; C12N 15/62

[52] U.S. Cl. ...................... 435/194; 536/23.2; 536/23.4; 435/320.1; 435/325; 435/419; 435/252.3; 435/252.33

[58] Field of Search ............................... 435/194, 320.1, 435/325, 419, 252.3, 252.33; 536/23.2, 23.4

[56] References Cited

FOREIGN PATENT DOCUMENTS 5304964  11/1993  Japan .

OTHER PUBLICATIONS

White et al., *Antonie van Leeuwenhoek*, vol. 64 (3/4), pp. 357–386, 1994, abstract only.

Hensel et al., *Syst. Appl. Microb.*, 11(3):312–319, 1989, abstract only.

Scholz et al., *Syst. Appl. Microbiol.*, 9(2–3):91–96, 1987, abstract only.

P. D. Gutman and K. W. Minton "Conserved sites in the 5'–3' exonuclease domain of *Escherichia coli* DNA polymerase" *Nucl. Acids Res.* 21:4406–4407 (1993).

M. Delarue, et al. "An attempt to unify the structure of polymerases" *Prot. Eng.* 3:461–467 (1990).

L. Blanco, et al. "A general structure for DNA–dependent DNA polymerases" *Gene* 100:27–38 (1991).

M. G. Riggs, et al. "Construction of single amino acid substitution mutants ofo cloned *Bacillus stearothermophilus* DNA polymerase I which lack 5'–3' exonuclease activity" *Biochim. Biophys. Acta* 1307:178–186 (1996).

A. Diaz, et al. "Streptococcus pneumoniae DNA Polymerase I Lacks 3'–5' Exonuclease Activity: Localization of the 5'–3' Exonucleolytic Domain" *J. Bacteriol.* 174:2014–2024 (1992, Mar.).

F. C. Lawyer, et al. "High–level Expression, PUrification, and Enzymatic Characterization of Full–length Thermus aquaticus DNA Polymerase and a Truncated Form Deficient in 5'–3' Exonuclease Activity" *PCR Mtds. Appl.* 2:275–287 (1993).

A. M. Phang, et al. "Cloning and complete sequence of the DNA polymerase–encoding gene (BstpolI) and characterisation of the Klenow–like fragment from *Bacillus stearothermophilus*" *Gene* 163:65–68 (1995).

T. Uemori, et al. "Cloning of the DNA Polymerase Gene of *Bacillus caldotenax* Characterization of the Gene Product" *J. Biochem.* 113:401–410 (1993).

*Primary Examiner*—Keith D. Hendricks
*Attorney, Agent, or Firm*—Donna R. Fugit

[57] ABSTRACT

A novel Type I DNA polymerase derived from *Bacillus pallidus* is provided. The gene encoding the polymerase has been cloned and expressed. Characterization of the enzyme revealed, in addition to DNA polymerase activity, 5'-3' exonuclease activity, reverse transcriptase activity, strand displacing activity and the ability to initiate polymerization at a nick in double-stranded DNA. In certain constructs the domain encoding the 5'-3' exonuclease activity is deleted to provide an enzyme which is particularly useful for Strand Displacement Amplification.

21 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TGCCAATCTA GAAGGCGTGC CSGGCRTCGG KRAAAARAC     39

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CACCAAGGAT CCS Y TTTTAT TTSGCGTCRT ACCA Y GT     37

( 2 ) INFORMATION FOR SEQ ID NO:3:

( i ) SEQUENCE CHARACTERISTICS:
        ( A ) LENGTH: 2631 base pairs
        ( B ) TYPE: nucleic acid
        ( C ) STRANDEDNESS: double
        ( D ) TOPOLOGY: linear ( i x ) FEATURE:
    ( A ) NAME/KEY: CDS
    ( B ) LOCATION: 1..2628

( x i ) SEQUENCE DESCRIPTION: SEQ ID NO:3:

| GTG | ACA | AAG | AAG | CTA | GTT | TTA | ATT | GAT | GGA | AAC | AGT | ATT | GCT | TAC | AGA | 48 |
|---|---|---|---|---|---|---|---|---|---|---|---|---|---|---|---|---|
| Val | Thr | Lys | Lys | Leu | Val | Leu | Ile | Asp | Gly | Asn | Ser | Ile | Ala | Tyr | Arg | |
| 1 | | | | 5 | | | | | 10 | | | | | 15 | | |

| GCG | TTT | TTC | GCT | TTG | CCG | CTT | TTA | AAT | AAT | GAT | AAG | GGG | ATT | TAT | ACG | 96 |
|---|---|---|---|---|---|---|---|---|---|---|---|---|---|---|---|---|
| Ala | Phe | Phe | Ala | Leu | Pro | Leu | Leu | Asn | Asn | Asp | Lys | Gly | Ile | Tyr | Thr | |
| | | | 20 | | | | | 25 | | | | | 30 | | | |

| AAT | GCA | ATT | TAC | GGC | TTT | ACA | AAT | ATG | CTG | TTA | AAA | GTA | CTG | GAG | GAA | 144 |
|---|---|---|---|---|---|---|---|---|---|---|---|---|---|---|---|---|
| Asn | Ala | Ile | Tyr | Gly | Phe | Thr | Asn | Met | Leu | Leu | Lys | Val | Leu | Glu | Glu | |
| | | 35 | | | | | 40 | | | | | 45 | | | | |

| GAA | AAA | CCG | ACA | CAT | ATT | CTT | GTT | GCA | TTT | GAT | GCA | GGG | AAA | ACA | ACG | 192 |
|---|---|---|---|---|---|---|---|---|---|---|---|---|---|---|---|---|
| Glu | Lys | Pro | Thr | His | Ile | Leu | Val | Ala | Phe | Asp | Ala | Gly | Lys | Thr | Thr | |
| 50 | | | | | 55 | | | | | 60 | | | | | | |

| TTC | CGG | CAT | AAA | ACT | TTT | AAA | GAA | TAT | AAA | GGA | ACT | CGG | CAA | AAA | ACC | 240 |
|---|---|---|---|---|---|---|---|---|---|---|---|---|---|---|---|---|
| Phe | Arg | His | Lys | Thr | Phe | Lys | Glu | Tyr | Lys | Gly | Thr | Arg | Gln | Lys | Thr | |
| 65 | | | | 70 | | | | | 75 | | | | | 80 | | |

| CCG | CCT | GAA | TTG | TCG | GAG | CAG | CTA | CCA | TTT | ATA | CGG | GAT | TTG | CTT | GAT | 288 |
|---|---|---|---|---|---|---|---|---|---|---|---|---|---|---|---|---|
| Pro | Pro | Glu | Leu | Ser | Glu | Gln | Leu | Pro | Phe | Ile | Arg | Asp | Leu | Leu | Asp | |
| | | | | 85 | | | | | 90 | | | | | 95 | | |

| GCC | TAC | CAA | ATT | ACA | ACA | TAT | GAA | CTC | GAA | AAT | TAT | GAG | GCT | GAT | GAT | 336 |
|---|---|---|---|---|---|---|---|---|---|---|---|---|---|---|---|---|
| Ala | Tyr | Gln | Ile | Thr | Thr | Tyr | Glu | Leu | Glu | Asn | Tyr | Glu | Ala | Asp | Asp | |
| | | | 100 | | | | | 105 | | | | | 110 | | | |

| ATT | ATT | GGA | ACA | GTT | GCG | AGA | CAA | GCT | GAG | AAG | CAA | GAT | TTT | GAA | GTG | 384 |
|---|---|---|---|---|---|---|---|---|---|---|---|---|---|---|---|---|
| Ile | Ile | Gly | Thr | Val | Ala | Arg | Gln | Ala | Glu | Lys | Gln | Asp | Phe | Glu | Val | |
| | | 115 | | | | | 120 | | | | | 125 | | | | |

| AAA | ATT | ATT | TCC | GGA | GAT | AAG | GAT | TTA | ACA | CAG | CTG | GCA | ACT | GAA | AAA | 432 |
|---|---|---|---|---|---|---|---|---|---|---|---|---|---|---|---|---|
| Lys | Ile | Ile | Ser | Gly | Asp | Lys | Asp | Leu | Thr | Gln | Leu | Ala | Thr | Glu | Lys | |
| | 130 | | | | | 135 | | | | | 140 | | | | | |

| ACG | ACC | GTT | TCC | ATC | ACG | AAA | AAA | GGA | ATT | ACA | GAT | GTT | GAA | CCG | CAC | 480 |
|---|---|---|---|---|---|---|---|---|---|---|---|---|---|---|---|---|
| Thr | Thr | Val | Ser | Ile | Thr | Lys | Lys | Gly | Ile | Thr | Asp | Val | Glu | Pro | His | |
| 145 | | | | | 150 | | | | | 155 | | | | | 160 | |

| ACG | CCT | GAA | TCG | ATT | CAA | GAG | AAG | TAT | GGG | CTA | AGC | CCG | GCA | CAA | ATT | 528 |
|---|---|---|---|---|---|---|---|---|---|---|---|---|---|---|---|---|
| Thr | Pro | Glu | Ser | Ile | Gln | Glu | Lys | Tyr | Gly | Leu | Ser | Pro | Ala | Gln | Ile | |
| | | | | 165 | | | | | 170 | | | | | 175 | | |

| ATT | GAT | TTG | AAA | GGA | TTG | ATG | GGC | GAT | CAA | TCA | GAT | AAT | ATC | CCA | GGT | 576 |
|---|---|---|---|---|---|---|---|---|---|---|---|---|---|---|---|---|
| Ile | Asp | Leu | Lys | Gly | Leu | Met | Gly | Asp | Gln | Ser | Asp | Asn | Ile | Pro | Gly | |
| | | | 180 | | | | | 185 | | | | | 190 | | | |

| GTG | CCC | GGC | GTT | GGA | GAG | AAA | ACC | GCG | ATT | AAA | TTG | CTG | AAA | CAG | TTT | 624 |
|---|---|---|---|---|---|---|---|---|---|---|---|---|---|---|---|---|
| Val | Pro | Gly | Val | Gly | Glu | Lys | Thr | Ala | Ile | Lys | Leu | Leu | Lys | Gln | Phe | |
| | | 195 | | | | | 200 | | | | | 205 | | | | |

| GAG | ACA | GTC | GAA | AAT | ATT | TTA | AAT | TCG | ATT | GAA | GAA | GTA | AAT | GGA | AAA | 672 |
|---|---|---|---|---|---|---|---|---|---|---|---|---|---|---|---|---|
| Glu | Thr | Val | Glu | Asn | Ile | Leu | Asn | Ser | Ile | Glu | Glu | Val | Asn | Gly | Lys | |
| | 210 | | | | | 215 | | | | | 220 | | | | | |

| AAA | TTG | AAG | GAA | AAC | TTA | CAA | AAC | TAT | AAA | GAG | CAA | GCA | TTA | ATG | AGC | 720 |
|---|---|---|---|---|---|---|---|---|---|---|---|---|---|---|---|---|
| Lys | Leu | Lys | Glu | Asn | Leu | Gln | Asn | Tyr | Lys | Glu | Gln | Ala | Leu | Met | Ser | |
| 225 | | | | | 230 | | | | | 235 | | | | | 240 | |

| AAA | CAG | CTT | GCG | ACA | ATT | CAT | TGT | GAA | GCT | CCT | GTC | GAA | ATA | AAA | ATT | 768 |
|---|---|---|---|---|---|---|---|---|---|---|---|---|---|---|---|---|
| Lys | Gln | Leu | Ala | Thr | Ile | His | Cys | Glu | Ala | Pro | Val | Glu | Ile | Lys | Ile | |
| | | | | 245 | | | | | 250 | | | | | 255 | | |

| CAA | GAC | CTT | GAG | TAT | AAA | GGC | TAT | GAC | AAA | GAA | AAA | GTA | GTG | AAA | ATT | 816 |
|---|---|---|---|---|---|---|---|---|---|---|---|---|---|---|---|---|
| Gln | Asp | Leu | Glu | Tyr | Lys | Gly | Tyr | Asp | Lys | Glu | Lys | Val | Val | Lys | Ile | |
| | | | 260 | | | | | 265 | | | | | 270 | | | |

| TTT | AAG | GAA | CTA | GGC | TTC | CAA | TCG | CTC | CTA | GAC | AAA | ATG | GGA | GAG | CAT | 864 |
|---|---|---|---|---|---|---|---|---|---|---|---|---|---|---|---|---|
| Phe | Lys | Glu | Leu | Gly | Phe | Gln | Ser | Leu | Leu | Asp | Lys | Met | Gly | Glu | His | |
| | | 275 | | | | | 280 | | | | | 285 | | | | |

| GAG | AAT | GAA | GAA | GCG | GAT | GAA | ATG | CCG | ACG | ATT | AAG | TTC | GAA | AAA | GTT | 912 |
|---|---|---|---|---|---|---|---|---|---|---|---|---|---|---|---|---|
| Glu | Asn | Glu | Glu | Ala | Asp | Glu | Met | Pro | Thr | Ile | Lys | Phe | Glu | Lys | Val | |

-continued

```
              290                          295                          300
GAA  AAG  CTG  TCA  GAC  AAG  GTT  TTA  TCA  GAG  AAG  GCA  GCT  CTT  TTA  GTG         960
Glu  Lys  Leu  Ser  Asp  Lys  Val  Leu  Ser  Glu  Lys  Ala  Ala  Leu  Leu  Val
305                 310                      315                           320

GAA  ATC  ATT  GAT  GAA  AAT  TAT  CAT  ACT  GGA  GAA  ATC  ATC  GGG  TTT  TCT        1008
Glu  Ile  Ile  Asp  Glu  Asn  Tyr  His  Thr  Gly  Glu  Ile  Ile  Gly  Phe  Ser
                         325                      330                      335

ATC  GCA  AAC  GAA  AAT  GGA  TGT  TTT  TAT  ATT  CCA  GCC  GAA  ATT  GCG  CTA        1056
Ile  Ala  Asn  Glu  Asn  Gly  Cys  Phe  Tyr  Ile  Pro  Ala  Glu  Ile  Ala  Leu
               340                      345                      350

CAT  TCA  AAA  GAG  TTC  ATA  GAA  TGG  GTG  AAG  GAT  GAA  ACA  AAG  CGG  AAA        1104
His  Ser  Lys  Glu  Phe  Ile  Glu  Trp  Val  Lys  Asp  Glu  Thr  Lys  Arg  Lys
               355                      360                      365

GTG  GTG  TAT  GAT  GCG  AAA  AAA  TCA  ATT  GTG  GCG  CTG  CGC  TGG  CGA  AAC        1152
Val  Val  Tyr  Asp  Ala  Lys  Lys  Ser  Ile  Val  Ala  Leu  Arg  Trp  Arg  Asn
     370                      375                      380

ATT  GAT  TTA  GCA  GGT  ATT  GAG  TTT  GAT  GTT  CTC  ATT  GCC  TCA  TAC  ATT        1200
Ile  Asp  Leu  Ala  Gly  Ile  Glu  Phe  Asp  Val  Leu  Ile  Ala  Ser  Tyr  Ile
385                      390                      395                      400

TTA  AAT  CCG  TCT  GAA  TCG  ATT  GAC  GAC  ATA  GCC  GAG  CTT  GCC  AAG  ACA        1248
Leu  Asn  Pro  Ser  Glu  Ser  Ile  Asp  Asp  Ile  Ala  Glu  Leu  Ala  Lys  Thr
                         405                      410                      415

AAA  AAT  AAA  CAT  TTA  GTT  CAA  AAG  GAT  GAA  GTG  ATT  TAC  GGA  AAA  GGC        1296
Lys  Asn  Lys  His  Leu  Val  Gln  Lys  Asp  Glu  Val  Ile  Tyr  Gly  Lys  Gly
               420                      425                      430

GCT  AAA  CGT  CAT  ATC  CCT  GAT  GAA  GAC  ATT  TTA  GGC  GAA  CAT  CTT  GCC        1344
Ala  Lys  Arg  His  Ile  Pro  Asp  Glu  Asp  Ile  Leu  Gly  Glu  His  Leu  Ala
               435                      440                      445

AGA  AAA  GCG  TTA  GCC  ATT  TAT  GAG  CTG  GAA  GAA  TTA  TTA  ATA  CAA  GAA        1392
Arg  Lys  Ala  Leu  Ala  Ile  Tyr  Glu  Leu  Glu  Glu  Leu  Leu  Ile  Gln  Glu
450                      455                      460

TTA  GAA  GAA  AAT  GAA  CAA  TTT  CAT  TTA  TTC  AGC  GAA  TTG  GAG  CTT  CCG        1440
Leu  Glu  Glu  Asn  Glu  Gln  Phe  His  Leu  Phe  Ser  Glu  Leu  Glu  Leu  Pro
465                      470                      475                      480

CTG  TCA  GCC  ATT  TTA  TCT  GAC  ATG  GAA  ACA  ACA  GGA  GTA  AAG  ATA  GAC        1488
Leu  Ser  Ala  Ile  Leu  Ser  Asp  Met  Glu  Thr  Thr  Gly  Val  Lys  Ile  Asp
                    485                      490                      495

GTC  AAC  CGT  CTG  AAA  GAA  ATG  GGA  AAA  GAG  CTT  GAT  GAA  CAG  CTG  AAG        1536
Val  Asn  Arg  Leu  Lys  Glu  Met  Gly  Lys  Glu  Leu  Asp  Glu  Gln  Leu  Lys
               500                      505                      510

CAA  TTA  GAA  AAG  GAT  ATT  CAT  CGT  CTA  GCT  GGA  GTG  TCA  TTT  AAC  ATT        1584
Gln  Leu  Glu  Lys  Asp  Ile  His  Arg  Leu  Ala  Gly  Val  Ser  Phe  Asn  Ile
          515                      520                      525

AAT  TCT  CCG  AAG  CAG  CTT  GGG  CCG  ATT  TTA  TTT  GAA  AAG  CTC  AAT  CTA        1632
Asn  Ser  Pro  Lys  Gln  Leu  Gly  Pro  Ile  Leu  Phe  Glu  Lys  Leu  Asn  Leu
     530                      535                      540

CCG  GTT  TTG  AAA  AAG  ACC  AAA  ACG  GGG  TAT  TCG  ACC  TCT  GCG  GAC  GTT        1680
Pro  Val  Leu  Lys  Lys  Thr  Lys  Thr  Gly  Tyr  Ser  Thr  Ser  Ala  Asp  Val
545                      550                      555                      560

TTA  GAA  AAA  TTG  AGA  GGA  CAG  CAC  GAA  ATT  GTG  GAG  AAA  ATT  TTG  CAT        1728
Leu  Glu  Lys  Leu  Arg  Gly  Gln  His  Glu  Ile  Val  Glu  Lys  Ile  Leu  His
                    565                      570                      575

TAC  CGG  CAG  CTC  GGA  AAG  CTT  CAA  TCG  ACG  TAT  ATT  GAA  GGG  CTG  CTG        1776
Tyr  Arg  Gln  Leu  Gly  Lys  Leu  Gln  Ser  Thr  Tyr  Ile  Glu  Gly  Leu  Leu
               580                      585                      590

AAG  GTT  GTC  CAT  CGT  GAT  ACG  CAT  AAA  ATC  CAC  ACC  CGA  TTT  AAT  CAA        1824
Lys  Val  Val  His  Arg  Asp  Thr  His  Lys  Ile  His  Thr  Arg  Phe  Asn  Gln
          595                      600                      605

GCA  TTA  ACG  CAA  ACC  GGA  AGA  TTA  AGC  TCC  ACA  GAC  CCG  AAT  TTG  CAA        1872
Ala  Leu  Thr  Gln  Thr  Gly  Arg  Leu  Ser  Ser  Thr  Asp  Pro  Asn  Leu  Gln
```

```
                    610                           615                           620
AAC   ATT   CCG   ATT   CGC   CTT   GAG   GAA   GGC   CGC   AAA   ATT   CGT   CAA   GCA   TTT        1920
Asn   Ile   Pro   Ile   Arg   Leu   Glu   Glu   Gly   Arg   Lys   Ile   Arg   Gln   Ala   Phe
625                           630                           635                           640

ATC   CCT   TCT   GAA   AAA   GAT   TGG   GTC   ATT   TTT   GCA   GCG   GAC   TAT   TCC   CAG        1968
Ile   Pro   Ser   Glu   Lys   Asp   Trp   Val   Ile   Phe   Ala   Ala   Asp   Tyr   Ser   Gln
                          645                           650                           655

ATT   GAA   CTG   CGA   GTG   CTT   GCG   CAT   ATA   TCT   GGA   GAT   GAA   AAA   TTG   ATT        2016
Ile   Glu   Leu   Arg   Val   Leu   Ala   His   Ile   Ser   Gly   Asp   Glu   Lys   Leu   Ile
                  660                           665                           670

GAA   GCG   TTT   AAA   CAA   GAT   CTT   GAT   ATT   CAT   ACA   AAA   ACG   GCG   ATC   GAT        2064
Glu   Ala   Phe   Lys   Gln   Asp   Leu   Asp   Ile   His   Thr   Lys   Thr   Ala   Ile   Asp
            675                           680                           685

GTG   TTC   CAT   GTC   GAA   GAA   GAT   AAA   GTG   ACC   TCC   AAC   ATG   AGA   AGA   CAG        2112
Val   Phe   His   Val   Glu   Glu   Asp   Lys   Val   Thr   Ser   Asn   Met   Arg   Arg   Gln
      690                           695                           700

GCA   AAA   GCA   GTT   AAT   TTC   GGG   ATT   GTT   TAC   GGA   ATC   AGC   GAT   TAC   GGA        2160
Ala   Lys   Ala   Val   Asn   Phe   Gly   Ile   Val   Tyr   Gly   Ile   Ser   Asp   Tyr   Gly
705                           710                           715                           720

TTG   TCG   CAA   AAC   TTA   GGA   ATT   ACC   CGA   AAA   GAA   GCT   GGT   GAA   TTT   ATT        2208
Leu   Ser   Gln   Asn   Leu   Gly   Ile   Thr   Arg   Lys   Glu   Ala   Gly   Glu   Phe   Ile
                          725                           730                           735

AAA   AAA   TAT   TTT   GAA   ATT   TAT   AAA   GGC   GTT   AAA   GAA   TAT   ATG   GAT   GGC        2256
Lys   Lys   Tyr   Phe   Glu   Ile   Tyr   Lys   Gly   Val   Lys   Glu   Tyr   Met   Asp   Gly
                  740                           745                           750

ATA   ATC   CAA   GAG   GCG   AAG   CAA   AAA   GGC   TAT   GTA   ACG   ACA   CTA   ATG   CAG        2304
Ile   Ile   Gln   Glu   Ala   Lys   Gln   Lys   Gly   Tyr   Val   Thr   Thr   Leu   Met   Gln
            755                           760                           765

CGT   CGG   AGA   TAT   ATT   CCG   GAA   ATT   ACG   AGC   AGA   AAT   TTC   AAT   ATC   AGA        2352
Arg   Arg   Arg   Tyr   Ile   Pro   Glu   Ile   Thr   Ser   Arg   Asn   Phe   Asn   Ile   Arg
770                           775                           780

AGC   TTC   GCT   GAG   CGA   ACA   GCC   ATG   AAT   ACT   CCG   ATT   CAA   GGA   AGT   GCA        2400
Ser   Phe   Ala   Glu   Arg   Thr   Ala   Met   Asn   Thr   Pro   Ile   Gln   Gly   Ser   Ala
785                           790                           795                           800

GCG   GAT   ATT   ATC   AAA   AAA   GCG   ATG   ATC   GAT   ATG   GCG   CAA   GAA   ATT   GAA        2448
Ala   Asp   Ile   Ile   Lys   Lys   Ala   Met   Ile   Asp   Met   Ala   Gln   Glu   Ile   Glu
                          805                           810                           815

AAA   CGA   AAT   TTG   CAA   ACG   AGG   CTG   CTG   CTT   CAA   GTT   CAT   GAC   GAA   TTG        2496
Lys   Arg   Asn   Leu   Gln   Thr   Arg   Leu   Leu   Leu   Gln   Val   His   Asp   Glu   Leu
                  820                           825                           830

GTG   TTT   GAA   GCG   CCA   AAG   GAT   GAA   ATT   GAA   ATT   TTA   GAA   AAG   CTT   GTT        2544
Val   Phe   Glu   Ala   Pro   Lys   Asp   Glu   Ile   Glu   Ile   Leu   Glu   Lys   Leu   Val
            835                           840                           845

CCG   GAA   GTA   ATG   GAA   AAT   GCC   ATT   CAG   CTA   AAA   GTA   CCG   TTA   AAG   GTT        2592
Pro   Glu   Val   Met   Glu   Asn   Ala   Ile   Gln   Leu   Lys   Val   Pro   Leu   Lys   Val
850                           855                           860

GAT   TAT   TCT   TAC   GGT   TCT   ACG   TGG   TAT   GAA   GCG   AAA   TAA                          2631
Asp   Tyr   Ser   Tyr   Gly   Ser   Thr   Trp   Tyr   Glu   Ala   Lys
865                           870                           875
```

( 2 ) INFORMATION FOR SEQ ID NO:4:

( i ) SEQUENCE CHARACTERISTICS:
        ( A ) LENGTH: 876 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Val   Thr   Lys   Lys   Leu   Val   Leu   Ile   Asp   Gly   Asn   Ser   Ile   Ala   Tyr   Arg
1                 5                             10                            15
```

-continued

| | | | | | | | | | | | | | |
|---|---|---|---|---|---|---|---|---|---|---|---|---|---|
|Ala|Phe|Phe|Ala|Leu|Pro|Leu|Leu|Asn|Asn|Asp|Lys|Gly|Ile|Tyr|Thr
| | | |20| | |25| | | |30| | |
|Asn|Ala|Ile|Tyr|Gly|Phe|Thr|Asn|Met|Leu|Leu|Lys|Val|Leu|Glu|Glu
| | |35| | | |40| | | |45| | |
|Glu|Lys|Pro|Thr|His|Ile|Leu|Val|Ala|Phe|Asp|Ala|Gly|Lys|Thr|Thr
| |50| | | |55| | | |60| | |
|Phe|Arg|His|Lys|Thr|Phe|Lys|Glu|Tyr|Lys|Gly|Thr|Arg|Gln|Lys|Thr
|65| | | |70| | | |75| | | |80
|Pro|Pro|Glu|Leu|Ser|Glu|Gln|Leu|Pro|Phe|Ile|Arg|Asp|Leu|Leu|Asp
| | | |85| | | |90| | | |95
|Ala|Tyr|Gln|Ile|Thr|Thr|Tyr|Glu|Leu|Glu|Asn|Tyr|Glu|Ala|Asp|Asp
| | |100| | | |105| | | |110
|Ile|Ile|Gly|Thr|Val|Ala|Arg|Gln|Ala|Glu|Lys|Gln|Asp|Phe|Glu|Val
| | |115| | | |120| | | |125
|Lys|Ile|Ile|Ser|Gly|Asp|Lys|Asp|Leu|Thr|Gln|Leu|Ala|Thr|Glu|Lys
| |130| | | |135| | | |140
|Thr|Thr|Val|Ser|Ile|Thr|Lys|Lys|Gly|Ile|Thr|Asp|Val|Glu|Pro|His
|145| | | |150| | | |155| | | |160
|Thr|Pro|Glu|Ser|Ile|Gln|Glu|Lys|Tyr|Gly|Leu|Ser|Pro|Ala|Gln|Ile
| | | |165| | | |170| | | |175
|Ile|Asp|Leu|Lys|Gly|Leu|Met|Gly|Asp|Gln|Ser|Asp|Asn|Ile|Pro|Gly
| | |180| | | |185| | | |190
|Val|Pro|Gly|Val|Gly|Glu|Lys|Thr|Ala|Ile|Lys|Leu|Leu|Lys|Gln|Phe
| | |195| | | |200| | | |205
|Glu|Thr|Val|Glu|Asn|Ile|Leu|Asn|Ser|Ile|Glu|Glu|Val|Asn|Gly|Lys
| | |210| | | |215| | | |220
|Lys|Leu|Lys|Glu|Asn|Leu|Gln|Asn|Tyr|Lys|Glu|Gln|Ala|Leu|Met|Ser
|225| | | |230| | | |235| | | |240
|Lys|Gln|Leu|Ala|Thr|Ile|His|Cys|Glu|Ala|Pro|Val|Glu|Ile|Lys|Ile
| | | |245| | | |250| | | |255
|Gln|Asp|Leu|Glu|Tyr|Lys|Gly|Tyr|Asp|Lys|Glu|Lys|Val|Val|Lys|Ile
| | |260| | | |265| | | |270
|Phe|Lys|Glu|Leu|Gly|Phe|Gln|Ser|Leu|Leu|Asp|Lys|Met|Gly|Glu|His
| |275| | | |280| | | |285
|Glu|Asn|Glu|Glu|Ala|Asp|Glu|Met|Pro|Thr|Ile|Lys|Phe|Glu|Lys|Val
| |290| | | |295| | | |300
|Glu|Lys|Leu|Ser|Asp|Lys|Val|Leu|Ser|Glu|Lys|Ala|Ala|Leu|Leu|Val
|305| | | |310| | | |315| | | |320
|Glu|Ile|Ile|Asp|Glu|Asn|Tyr|His|Thr|Gly|Glu|Ile|Ile|Gly|Phe|Ser
| | | |325| | | |330| | | |335
|Ile|Ala|Asn|Glu|Asn|Gly|Cys|Phe|Tyr|Ile|Pro|Ala|Glu|Ile|Ala|Leu
| | |340| | | |345| | | |350
|His|Ser|Lys|Glu|Phe|Ile|Glu|Trp|Val|Lys|Asp|Glu|Thr|Lys|Arg|Lys
| |355| | | |360| | | |365
|Val|Val|Tyr|Asp|Ala|Lys|Lys|Ser|Ile|Val|Ala|Leu|Arg|Trp|Arg|Asn
| |370| | | |375| | | |380
|Ile|Asp|Leu|Ala|Gly|Ile|Glu|Phe|Asp|Val|Leu|Ile|Ala|Ser|Tyr|Ile
|385| | | |390| | | |395| | | |400
|Leu|Asn|Pro|Ser|Glu|Ser|Ile|Asp|Asp|Ile|Ala|Glu|Leu|Ala|Lys|Thr
| | | |405| | | |410| | | |415
|Lys|Asn|Lys|His|Leu|Val|Gln|Lys|Asp|Glu|Val|Ile|Tyr|Gly|Lys|Gly
| | |420| | | |425| | | |430
|Ala|Lys|Arg|His|Ile|Pro|Asp|Glu|Asp|Ile|Leu|Gly|Glu|His|Leu|Ala

-continued

|     |     |     | 435 |     |     |     | 440 |     |     |     | 445 |     |     |     |
|---|---|---|---|---|---|---|---|---|---|---|---|---|---|---|

Arg Lys Ala Leu Ala Ile Tyr Glu Leu Glu Glu Leu Leu Ile Gln Glu
        450                 455                 460

Leu Glu Glu Asn Glu Gln Phe His Leu Phe Ser Glu Leu Glu Leu Pro
465                 470                 475                 480

Leu Ser Ala Ile Leu Ser Asp Met Glu Thr Thr Gly Val Lys Ile Asp
                485                 490                 495

Val Asn Arg Leu Lys Glu Met Gly Lys Glu Leu Asp Glu Gln Leu Lys
            500                 505                 510

Gln Leu Glu Lys Asp Ile His Arg Leu Ala Gly Val Ser Phe Asn Ile
        515                 520                 525

Asn Ser Pro Lys Gln Leu Gly Pro Ile Leu Phe Glu Lys Leu Asn Leu
530                 535                 540

Pro Val Leu Lys Lys Thr Lys Thr Gly Tyr Ser Thr Ser Ala Asp Val
545                 550                 555                 560

Leu Glu Lys Leu Arg Gly Gln His Glu Ile Val Glu Lys Ile Leu His
                565                 570                 575

Tyr Arg Gln Leu Gly Lys Leu Gln Ser Thr Tyr Ile Glu Gly Leu Leu
            580                 585                 590

Lys Val Val His Arg Asp Thr His Lys Ile His Thr Arg Phe Asn Gln
        595                 600                 605

Ala Leu Thr Gln Thr Gly Arg Leu Ser Ser Thr Asp Pro Asn Leu Gln
        610                 615                 620

Asn Ile Pro Ile Arg Leu Glu Glu Gly Arg Lys Ile Arg Gln Ala Phe
625                 630                 635                 640

Ile Pro Ser Glu Lys Asp Trp Val Ile Phe Ala Ala Asp Tyr Ser Gln
            645                 650                 655

Ile Glu Leu Arg Val Leu Ala His Ile Ser Gly Asp Glu Lys Leu Ile
            660                 665                 670

Glu Ala Phe Lys Gln Asp Leu Asp Ile His Thr Lys Thr Ala Ile Asp
        675                 680                 685

Val Phe His Val Glu Glu Asp Lys Val Thr Ser Asn Met Arg Arg Gln
    690                 695                 700

Ala Lys Ala Val Asn Phe Gly Ile Val Tyr Gly Ile Ser Asp Tyr Gly
705                 710                 715                 720

Leu Ser Gln Asn Leu Gly Ile Thr Arg Lys Glu Ala Gly Glu Phe Ile
            725                 730                 735

Lys Lys Tyr Phe Glu Ile Tyr Lys Gly Val Lys Glu Tyr Met Asp Gly
            740                 745                 750

Ile Ile Gln Glu Ala Lys Gln Lys Gly Tyr Val Thr Thr Leu Met Gln
        755                 760                 765

Arg Arg Arg Tyr Ile Pro Glu Ile Thr Ser Arg Asn Phe Asn Ile Arg
770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Met Ala Gln Glu Ile Glu
                805                 810                 815

Lys Arg Asn Leu Gln Thr Arg Leu Leu Leu Gln Val His Asp Glu Leu
            820                 825                 830

Val Phe Glu Ala Pro Lys Asp Glu Ile Glu Ile Leu Glu Lys Leu Val
        835                 840                 845

Pro Glu Val Met Glu Asn Ala Ile Gln Leu Lys Val Pro Leu Lys Val
850                 855                 860

```
Asp Tyr Ser Tyr Gly Ser Thr Trp Tyr Glu Ala Lys
865                 870                 875
```

( 2 ) INFORMATION FOR SEQ ID NO:5:

( i ) SEQUENCE CHARACTERISTICS:
        ( A ) LENGTH: 3255 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..3252

( x i ) SEQUENCE DESCRIPTION: SEQ ID NO:5:

```
ATG AAA ATC GAA GAA GGT AAA CTG GTA ATC TGG ATT AAC GGC GAT AAA    48
Met Lys Ile Glu Glu Gly Lys Leu Val Ile Trp Ile Asn Gly Asp Lys
            880                 885                 890

GGC TAT AAC GGT CTC GCT GAA GTC GGT AAG AAA TTC GAG AAA GAT ACC    96
Gly Tyr Asn Gly Leu Ala Glu Val Gly Lys Lys Phe Glu Lys Asp Thr
            895                 900                 905

GGA ATT AAA GTC ACC GTT GAG CAT CCG GAT AAA CTG GAA GAG AAA TTC   144
Gly Ile Lys Val Thr Val Glu His Pro Asp Lys Leu Glu Glu Lys Phe
910                 915                 920

CCA CAG GTT GCG GCA ACT GGC GAT GGC CCT GAC ATT ATC TTC TGG GCA   192
Pro Gln Val Ala Ala Thr Gly Asp Gly Pro Asp Ile Ile Phe Trp Ala
925                 930                 935                 940

CAC GAC CGC TTT GGT GGC TAC GCT CAA TCT GGC CTG TTG GCT GAA ATC   240
His Asp Arg Phe Gly Gly Tyr Ala Gln Ser Gly Leu Leu Ala Glu Ile
                945                 950                 955

ACC CCG GAC AAA GCG TTC CAG GAC AAG CTG TAT CCG TTT ACC TGG GAT   288
Thr Pro Asp Lys Ala Phe Gln Asp Lys Leu Tyr Pro Phe Thr Trp Asp
            960                 965                 970

GCC GTA CGT TAC AAC GGC AAG CTG ATT GCT TAC CCG ATC GCT GTT GAA   336
Ala Val Arg Tyr Asn Gly Lys Leu Ile Ala Tyr Pro Ile Ala Val Glu
            975                 980                 985

GCG TTA TCG CTG ATT TAT AAC AAA GAT CTG CTG CCG AAC CCG CCA AAA   384
Ala Leu Ser Leu Ile Tyr Asn Lys Asp Leu Leu Pro Asn Pro Pro Lys
990                 995                 1000

ACC TGG GAA GAG ATC CCG GCG CTG GAT AAA GAA CTG AAA GCG AAA GGT   432
Thr Trp Glu Glu Ile Pro Ala Leu Asp Lys Glu Leu Lys Ala Lys Gly
1005                1010                1015                1020

AAG AGC GCG CTG ATG TTC AAC CTG CAA GAA CCG TAC TTC ACC TGG CCG   480
Lys Ser Ala Leu Met Phe Asn Leu Gln Glu Pro Tyr Phe Thr Trp Pro
                1025                1030                1035

CTG ATT GCT GCT GAC GGG GGT TAT GCG TTC AAG TAT GAA AAC GGC AAG   528
Leu Ile Ala Ala Asp Gly Gly Tyr Ala Phe Lys Tyr Glu Asn Gly Lys
                1040                1045                1050

TAC GAC ATT AAA GAC GTG GGC GTG GAT AAC GCT GGC GCG AAA GCG GGT   576
Tyr Asp Ile Lys Asp Val Gly Val Asp Asn Ala Gly Ala Lys Ala Gly
            1055                1060                1065

CTG ACC TTC CTG GTT GAC CTG ATT AAA AAC AAA CAC ATG AAT GCA GAC   624
Leu Thr Phe Leu Val Asp Leu Ile Lys Asn Lys His Met Asn Ala Asp
            1070                1075                1080

ACC GAT TAC TCC ATC GCA GAA GCT GCC TTT AAT AAA GGC GAA ACA GCG   672
Thr Asp Tyr Ser Ile Ala Glu Ala Ala Phe Asn Lys Gly Glu Thr Ala
1085                1090                1095                1100

ATG ACC ATC AAC GGC CCG TGG GCA TGG TCC AAC ATC GAC ACC AGC AAA   720
Met Thr Ile Asn Gly Pro Trp Ala Trp Ser Asn Ile Asp Thr Ser Lys
                1105                1110                1115

GTG AAT TAT GGT GTA ACG GTA CTG CCG ACC TTC AAG GGT CAA CCA TCC   768
Val Asn Tyr Gly Val Thr Val Leu Pro Thr Phe Lys Gly Gln Pro Ser
```

```
        1120                    1125                    1130

AAA CCG TTC GTT GGC GTG CTG AGC GCA GGT ATT AAC GCC GCC AGT CCG      816
Lys Pro Phe Val Gly Val Leu Ser Ala Gly Ile Asn Ala Ala Ser Pro
        1135                    1140                    1145

AAC AAA GAG CTG GCA AAA GAG TTC CTC GAA AAC TAT CTG CTG ACT GAT      864
Asn Lys Glu Leu Ala Lys Glu Phe Leu Glu Asn Tyr Leu Leu Thr Asp
        1150                    1155                    1160

GAA GGT CTG GAA GCG GTT AAT AAA GAC AAA CCG CTG GGT GCC GTA GCG      912
Glu Gly Leu Glu Ala Val Asn Lys Asp Lys Pro Leu Gly Ala Val Ala
1165                    1170                    1175                    1180

CTG AAG TCT TAC GAG GAA GAG TTG GCG AAA GAT CCA CGT ATT GCC GCC      960
Leu Lys Ser Tyr Glu Glu Glu Leu Ala Lys Asp Pro Arg Ile Ala Ala
                1185                    1190                    1195

ACC ATG GAA AAC GCC CAG AAA GGT GAA ATC ATG CCG AAC ATC CCG CAG     1008
Thr Met Glu Asn Ala Gln Lys Gly Glu Ile Met Pro Asn Ile Pro Gln
        1200                    1205                    1210

ATG TCC GCT TTC TGG TAT GCC GTG CGT ACT GCG GTG ATC AAC GCC GCC     1056
Met Ser Ala Phe Trp Tyr Ala Val Arg Thr Ala Val Ile Asn Ala Ala
        1215                    1220                    1225

AGC GGT CGT CAG ACT GTC GAT GAA GCC CTG AAA GAC GCG CAG ACT AAT     1104
Ser Gly Arg Gln Thr Val Asp Glu Ala Leu Lys Asp Ala Gln Thr Asn
        1230                    1235                    1240

TCG AGC TCG AAC AAC AAC AAC AAT AAC AAT AAC AAC AAC CTC GGG ATC     1152
Ser Ser Ser Asn Asn Asn Asn Asn Asn Asn Asn Asn Asn Leu Gly Ile
1245                    1250                    1255                    1260

GAG GGA AGG ATT TCA GAA TTC GGT GTG CCC GGC GTT GGA GAG AAA ACC     1200
Glu Gly Arg Ile Ser Glu Phe Gly Val Pro Gly Val Gly Glu Lys Thr
                1265                    1270                    1275

GCG ATT AAA TTG CTG AAA CAG TTT GAG ACA GTC GAA AAT ATT TTA AAT     1248
Ala Ile Lys Leu Leu Lys Gln Phe Glu Thr Val Glu Asn Ile Leu Asn
        1280                    1285                    1290

TCG ATT GAA GAA GTA AAT GGA AAA AAA TTG AAG GAA AAC TTA CAA AAC     1296
Ser Ile Glu Glu Val Asn Gly Lys Lys Leu Lys Glu Asn Leu Gln Asn
        1295                    1300                    1305

TAT AAA GAG CAA GCA TTA ATG AGC AAA CAG CTT GCG ACA ATT CAT TGT     1344
Tyr Lys Glu Gln Ala Leu Met Ser Lys Gln Leu Ala Thr Ile His Cys
        1310                    1315                    1320

GAA GCT CCT GTC GAA ATA AAA ATT CAA GAC CTT GAG TAT AAA GGC TAT     1392
Glu Ala Pro Val Glu Ile Lys Ile Gln Asp Leu Glu Tyr Lys Gly Tyr
1325                    1330                    1335                    1340

GAC AAA GAA AAA GTA GTG AAA ATT TTT AAG GAA CTA GGC TTC CAA TCG     1440
Asp Lys Glu Lys Val Val Lys Ile Phe Lys Glu Leu Gly Phe Gln Ser
                1345                    1350                    1355

CTC CTA GAC AAA ATG GGA GAG CAT GAG AAT GAA GAA GCG GAT GAA ATG     1488
Leu Leu Asp Lys Met Gly Glu His Glu Asn Glu Glu Ala Asp Glu Met
        1360                    1365                    1370

CCG ACG ATT AAG TTC GAA AAA GTT GAA AAG CTG TCA GAC AAG GTT TTA     1536
Pro Thr Ile Lys Phe Glu Lys Val Glu Lys Leu Ser Asp Lys Val Leu
        1375                    1380                    1385

TCA GAG AAG GCA GCT CTT TTA GTG GAA ATC ATT GAT GAA AAT TAT CAT     1584
Ser Glu Lys Ala Ala Leu Leu Val Glu Ile Ile Asp Glu Asn Tyr His
        1390                    1395                    1400

ACT GGA GAA ATC ATC GGG TTT TCT ATC GCA AAC GAA AAT GGA TGT TTT     1632
Thr Gly Glu Ile Ile Gly Phe Ser Ile Ala Asn Glu Asn Gly Cys Phe
1405                    1410                    1415                    1420

TAT ATT CCA GCC GAA ATT GCG CTA CAT TCA AAA GAG TTC ATA GAA TGG     1680
Tyr Ile Pro Ala Glu Ile Ala Leu His Ser Lys Glu Phe Ile Glu Trp
                1425                    1430                    1435

GTG AAG GAT GAA ACA AAG CGG AAA GTG GTG TAT GAT GCG AAA AAA TCA     1728
Val Lys Asp Glu Thr Lys Arg Lys Val Val Tyr Asp Ala Lys Lys Ser
```

```
                    1440              1445                 1450
ATT GTG GCG CTG CGC TGG CGA AAC ATT GAT TTA GCA GGT ATT GAG TTT    1776
Ile Val Ala Leu Arg Trp Arg Asn Ile Asp Leu Ala Gly Ile Glu Phe
        1455              1460                 1465

GAT GTT CTC ATT GCC TCA TAC ATT TTA AAT CCG TCT GAA TCG ATT GAC    1824
Asp Val Leu Ile Ala Ser Tyr Ile Leu Asn Pro Ser Glu Ser Ile Asp
        1470              1475                 1480

GAC ATA GCC GAG CTT GCC AAG ACA AAA AAT AAA CAT TTA GTT CAA AAG    1872
Asp Ile Ala Glu Leu Ala Lys Thr Lys Asn Lys His Leu Val Gln Lys
1485             1490                 1495                 1500

GAT GAA GTG ATT TAC GGA AAA GGC GCT AAA CGT CAT ATC CCT GAT GAA    1920
Asp Glu Val Ile Tyr Gly Lys Gly Ala Lys Arg His Ile Pro Asp Glu
                 1505                 1510                 1515

GAC ATT TTA GGC GAA CAT CTT GCC AGA AAA GCG TTA GCC ATT TAT GAG    1968
Asp Ile Leu Gly Glu His Leu Ala Arg Lys Ala Leu Ala Ile Tyr Glu
        1520                 1525                 1530

CTG GAA GAA TTA TTA ATA CAA GAA TTA GAA GAA AAT GAA CAA TTT CAT    2016
Leu Glu Glu Leu Leu Ile Gln Glu Leu Glu Glu Asn Glu Gln Phe His
        1535                 1540                 1545

TTA TTC AGC GAA TTG GAG CTT CCG CTG TCA GCC ATT TTA TCT GAC ATG    2064
Leu Phe Ser Glu Leu Glu Leu Pro Leu Ser Ala Ile Leu Ser Asp Met
    1550                 1555                 1560

GAA ACA ACA GGA GTA AAG ATA GAC GTC AAC CGT CTG AAA GAA ATG GGA    2112
Glu Thr Thr Gly Val Lys Ile Asp Val Asn Arg Leu Lys Glu Met Gly
1565             1570                 1575                 1580

AAA GAG CTT GAT GAA CAG CTG AAG CAA TTA GAA AAG GAT ATT CAT CGT    2160
Lys Glu Leu Asp Glu Gln Leu Lys Gln Leu Glu Lys Asp Ile His Arg
                 1585                 1590                 1595

CTA GCT GGA GTG TCA TTT AAC ATT AAT TCT CCG AAG CAG CTT GGG CCG    2208
Leu Ala Gly Val Ser Phe Asn Ile Asn Ser Pro Lys Gln Leu Gly Pro
        1600                 1605                 1610

ATT TTA TTT GAA AAG CTC AAT CTA CCG GTT TTG AAA AAG ACC AAA ACG    2256
Ile Leu Phe Glu Lys Leu Asn Leu Pro Val Leu Lys Lys Thr Lys Thr
        1615                 1620                 1625

GGG TAT TCG ACC TCT GCG GAC GTT TTA GAA AAA TTG AGA GGA CAG CAC    2304
Gly Tyr Ser Thr Ser Ala Asp Val Leu Glu Lys Leu Arg Gly Gln His
        1630                 1635                 1640

GAA ATT GTG GAG AAA ATT TTG CAT TAC CGG CAG CTC GGA AAG CTT CAA    2352
Glu Ile Val Glu Lys Ile Leu His Tyr Arg Gln Leu Gly Lys Leu Gln
1645             1650                 1655                 1660

TCG ACG TAT ATT GAA GGG CTG CTG AAG GTT GTC CAT CGT GAT ACG CAT    2400
Ser Thr Tyr Ile Glu Gly Leu Leu Lys Val Val His Arg Asp Thr His
                 1665                 1670                 1675

AAA ATC CAC ACC CGA TTT AAT CAA GCA TTA ACG CAA ACC GGA AGA TTA    2448
Lys Ile His Thr Arg Phe Asn Gln Ala Leu Thr Gln Thr Gly Arg Leu
        1680                 1685                 1690

AGC TCC ACA GAC CCG AAT TTG CAA AAC ATT CCG ATT CGC CTT GAG GAA    2496
Ser Ser Thr Asp Pro Asn Leu Gln Asn Ile Pro Ile Arg Leu Glu Glu
        1695                 1700                 1705

GGC CGC AAA ATT CGT CAA GCA TTT ATC CCT TCT GAA AAA GAT TGG GTC    2544
Gly Arg Lys Ile Arg Gln Ala Phe Ile Pro Ser Glu Lys Asp Trp Val
        1710                 1715                 1720

ATT TTT GCA GCG GAC TAT TCC CAG ATT GAA CTG CGA GTG CTT GCG CAT    2592
Ile Phe Ala Ala Asp Tyr Ser Gln Ile Glu Leu Arg Val Leu Ala His
1725             1730                 1735                 1740

ATA TCT GGA GAT GAA AAA TTG ATT GAA GCG TTT AAA CAA GAT CTT GAT    2640
Ile Ser Gly Asp Glu Lys Leu Ile Glu Ala Phe Lys Gln Asp Leu Asp
                 1745                 1750                 1755

ATT CAT ACA AAA ACG GCG ATC GAT GTG TTC CAT GTC GAA GAA GAT AAA    2688
Ile His Thr Lys Thr Ala Ile Asp Val Phe His Val Glu Glu Asp Lys
```

|  |  |  |  |  |  |  |  |  |  |  |  |  |  |  |  |  |
|---|---|---|---|---|---|---|---|---|---|---|---|---|---|---|---|---|
| | 1760 | | | | | 1765 | | | | | 1770 | | | | | |
| GTG | ACC | TCC | AAC | ATG | AGA | AGA | CAG | GCA | AAA | GCA | GTT | AAT | TTC | GGG | ATT | 2736 |
| Val | Thr | Ser | Asn | Met | Arg | Arg | Gln | Ala | Lys | Ala | Val | Asn | Phe | Gly | Ile | |
| | | 1775 | | | | | 1780 | | | | | 1785 | | | | |
| GTT | TAC | GGA | ATC | AGC | GAT | TAC | GGA | TTG | TCG | CAA | AAC | TTA | GGA | ATT | ACC | 2784 |
| Val | Tyr | Gly | Ile | Ser | Asp | Tyr | Gly | Leu | Ser | Gln | Asn | Leu | Gly | Ile | Thr | |
| | 1790 | | | | | 1795 | | | | | 1800 | | | | | |
| CGA | AAA | GAA | GCT | GGT | GAA | TTT | ATT | AAA | AAA | TAT | TTT | GAA | ATT | TAT | AAA | 2832 |
| Arg | Lys | Glu | Ala | Gly | Glu | Phe | Ile | Lys | Lys | Tyr | Phe | Glu | Ile | Tyr | Lys | |
| 1805 | | | | | 1810 | | | | | 1815 | | | | | 1820 | |
| GGC | GTT | AAA | GAA | TAT | ATG | GAT | GGC | ATA | ATC | CAA | GAG | GCG | AAG | CAA | AAA | 2880 |
| Gly | Val | Lys | Glu | Tyr | Met | Asp | Gly | Ile | Ile | Gln | Glu | Ala | Lys | Gln | Lys | |
| | | | | 1825 | | | | | 1830 | | | | | 1835 | | |
| GGC | TAT | GTA | ACG | ACA | CTA | ATG | CAG | CGT | CGG | AGA | TAT | ATT | CCG | GAA | ATT | 2928 |
| Gly | Tyr | Val | Thr | Thr | Leu | Met | Gln | Arg | Arg | Arg | Tyr | Ile | Pro | Glu | Ile | |
| | | | 1840 | | | | | 1845 | | | | | 1850 | | | |
| ACG | AGC | AGA | AAT | TTC | AAT | ATC | AGA | AGC | TTC | GCT | GAG | CGA | ACA | GCC | ATG | 2976 |
| Thr | Ser | Arg | Asn | Phe | Asn | Ile | Arg | Ser | Phe | Ala | Glu | Arg | Thr | Ala | Met | |
| | | | | 1855 | | | | | 1860 | | | | | 1865 | | |
| AAT | ACT | CCG | ATT | CAA | GGA | AGT | GCA | GCG | GAT | ATT | ATC | AAA | AAA | GCG | ATG | 3024 |
| Asn | Thr | Pro | Ile | Gln | Gly | Ser | Ala | Ala | Asp | Ile | Ile | Lys | Lys | Ala | Met | |
| | 1870 | | | | | 1875 | | | | | 1880 | | | | | |
| ATC | GAT | ATG | GCG | CAA | GAA | ATT | GAA | AAA | CGA | AAT | TTG | CAA | ACG | AGG | CTG | 3072 |
| Ile | Asp | Met | Ala | Gln | Glu | Ile | Glu | Lys | Arg | Asn | Leu | Gln | Thr | Arg | Leu | |
| 1885 | | | | | 1890 | | | | | 1895 | | | | | 1900 | |
| CTG | CTT | CAA | GTT | CAT | GAC | GAA | TTG | GTG | TTT | GAA | GCG | CCA | AAG | GAT | GAA | 3120 |
| Leu | Leu | Gln | Val | His | Asp | Glu | Leu | Val | Phe | Glu | Ala | Pro | Lys | Asp | Glu | |
| | | | | 1905 | | | | | 1910 | | | | | 1915 | | |
| ATT | GAA | ATT | TTA | GAA | AAG | CTT | GTT | CCG | GAA | GTA | ATG | GAA | AAT | GCC | ATT | 3168 |
| Ile | Glu | Ile | Leu | Glu | Lys | Leu | Val | Pro | Glu | Val | Met | Glu | Asn | Ala | Ile | |
| | | | 1920 | | | | | 1925 | | | | | 1930 | | | |
| CAG | CTA | AAA | GTA | CCG | TTA | AAG | GTT | GAT | TAT | TCT | TAC | GGT | TCT | ACG | TGG | 3216 |
| Gln | Leu | Lys | Val | Pro | Leu | Lys | Val | Asp | Tyr | Ser | Tyr | Gly | Ser | Thr | Trp | |
| | | 1935 | | | | | 1940 | | | | | 1945 | | | | |
| TAT | GAC | GCC | AAA | TCA | TCT | CAT | CAT | CAT | CAT | CAT | TAA | | | | | 3255 |
| Tyr | Asp | Ala | Lys | Ser | Ser | His | His | His | His | His | | | | | | |
| 1950 | | | | | 1955 | | | | | 1960 | | | | | | |

( 2 ) INFORMATION FOR SEQ ID NO:6:

( i ) SEQUENCE CHARACTERISTICS:
        ( A ) LENGTH: 1084 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Lys | Ile | Glu | Glu | Gly | Lys | Leu | Val | Ile | Trp | Ile | Asn | Gly | Asp | Lys |
|---|---|---|---|---|---|---|---|---|---|---|---|---|---|---|---|
| 1 | | | | 5 | | | | | 10 | | | | | 15 | |
| Gly | Tyr | Asn | Gly | Leu | Ala | Glu | Val | Gly | Lys | Lys | Phe | Glu | Lys | Asp | Thr |
| | | | 20 | | | | | 25 | | | | | 30 | | |
| Gly | Ile | Lys | Val | Thr | Val | Glu | His | Pro | Asp | Lys | Leu | Glu | Glu | Lys | Phe |
| | | 35 | | | | | 40 | | | | | 45 | | | |
| Pro | Gln | Val | Ala | Ala | Thr | Gly | Asp | Gly | Pro | Asp | Ile | Ile | Phe | Trp | Ala |
| | 50 | | | | | 55 | | | | | 60 | | | | |
| His | Asp | Arg | Phe | Gly | Gly | Tyr | Ala | Gln | Ser | Gly | Leu | Leu | Ala | Glu | Ile |
| 65 | | | | | 70 | | | | | 75 | | | | | 80 |
| Thr | Pro | Asp | Lys | Ala | Phe | Gln | Asp | Lys | Leu | Tyr | Pro | Phe | Thr | Trp | Asp |
| | | | 85 | | | | | 90 | | | | | 95 | | |

```
Ala Val Arg Tyr Asn Gly Lys Leu Ile Ala Tyr Pro Ile Ala Val Glu
        100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
        290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Val Pro Gly Val Gly Glu Lys Thr
385                 390                 395                 400

Ala Ile Lys Leu Leu Lys Gln Phe Glu Thr Val Glu Asn Ile Leu Asn
                405                 410                 415

Ser Ile Glu Glu Val Asn Gly Lys Lys Leu Lys Glu Asn Leu Gln Asn
            420                 425                 430

Tyr Lys Glu Gln Ala Leu Met Ser Lys Gln Leu Ala Thr Ile His Cys
        435                 440                 445

Glu Ala Pro Val Glu Ile Lys Ile Gln Asp Leu Glu Tyr Lys Gly Tyr
    450                 455                 460

Asp Lys Glu Lys Val Val Lys Ile Phe Lys Glu Leu Gly Phe Gln Ser
465                 470                 475                 480

Leu Leu Asp Lys Met Gly Glu His Glu Asn Glu Glu Ala Asp Glu Met
                485                 490                 495

Pro Thr Ile Lys Phe Glu Lys Val Glu Lys Leu Ser Asp Lys Val Leu
            500                 505                 510

Ser Glu Lys Ala Ala Leu Leu Val Glu Ile Ile Asp Glu Asn Tyr His
        515                 520                 525
```

```
Thr Gly Glu Ile Ile Gly Phe Ser Ile Ala Asn Glu Asn Gly Cys Phe
    530             535             540
Tyr Ile Pro Ala Glu Ile Ala Leu His Ser Lys Glu Phe Ile Glu Trp
545             550             555                         560
Val Lys Asp Glu Thr Lys Arg Lys Val Val Tyr Asp Ala Lys Lys Ser
                565             570                     575
Ile Val Ala Leu Arg Trp Arg Asn Ile Asp Leu Ala Gly Ile Glu Phe
            580             585                     590
Asp Val Leu Ile Ala Ser Tyr Ile Leu Asn Pro Ser Glu Ser Ile Asp
        595             600             605
Asp Ile Ala Glu Leu Ala Lys Thr Lys Asn Lys His Leu Val Gln Lys
    610             615             620
Asp Glu Val Ile Tyr Gly Lys Gly Ala Lys Arg His Ile Pro Asp Glu
625             630             635                         640
Asp Ile Leu Gly Glu His Leu Ala Arg Lys Ala Leu Ala Ile Tyr Glu
            645             650                     655
Leu Glu Glu Leu Leu Ile Gln Glu Leu Glu Glu Asn Glu Gln Phe His
        660             665             670
Leu Phe Ser Glu Leu Glu Leu Pro Leu Ser Ala Ile Leu Ser Asp Met
    675             680             685
Glu Thr Thr Gly Val Lys Ile Asp Val Asn Arg Leu Lys Glu Met Gly
690             695             700
Lys Glu Leu Asp Glu Gln Leu Lys Gln Leu Glu Lys Asp Ile His Arg
705             710             715                         720
Leu Ala Gly Val Ser Phe Asn Ile Asn Ser Pro Lys Gln Leu Gly Pro
            725             730                     735
Ile Leu Phe Glu Lys Leu Asn Leu Pro Val Leu Lys Lys Thr Lys Thr
        740             745             750
Gly Tyr Ser Thr Ser Ala Asp Val Leu Glu Lys Leu Arg Gly Gln His
    755             760             765
Glu Ile Val Glu Lys Ile Leu His Tyr Arg Gln Leu Gly Lys Leu Gln
770             775             780
Ser Thr Tyr Ile Glu Gly Leu Leu Lys Val Val His Arg Asp Thr His
785             790             795                         800
Lys Ile His Thr Arg Phe Asn Gln Ala Leu Thr Gln Thr Gly Arg Leu
            805             810                     815
Ser Ser Thr Asp Pro Asn Leu Gln Asn Ile Pro Ile Arg Leu Glu Glu
        820             825             830
Gly Arg Lys Ile Arg Gln Ala Phe Ile Pro Ser Glu Lys Asp Trp Val
    835             840             845
Ile Phe Ala Ala Asp Tyr Ser Gln Ile Glu Leu Arg Val Leu Ala His
850             855             860
Ile Ser Gly Asp Glu Lys Leu Ile Glu Ala Phe Lys Gln Asp Leu Asp
865             870             875                         880
Ile His Thr Lys Thr Ala Ile Asp Val Phe His Val Glu Glu Asp Lys
            885             890                     895
Val Thr Ser Asn Met Arg Arg Gln Ala Lys Ala Val Asn Phe Gly Ile
        900             905             910
Val Tyr Gly Ile Ser Asp Tyr Gly Leu Ser Gln Asn Leu Gly Ile Thr
    915             920             925
Arg Lys Glu Ala Gly Glu Phe Ile Lys Lys Tyr Phe Glu Ile Tyr Lys
    930             935             940
Gly Val Lys Glu Tyr Met Asp Gly Ile Ile Gln Glu Ala Lys Gln Lys
```

-continued

```
945                    950                    955                    960
Gly Tyr Val Thr Thr Leu Met Gln Arg Arg Tyr Ile Pro Glu Ile
                965                    970                    975
Thr Ser Arg Asn Phe Asn Ile Arg Ser Phe Ala Glu Arg Thr Ala Met
                980                    985                    990
Asn Thr Pro Ile Gln Gly Ser Ala Ala Asp Ile Ile Lys Lys Ala Met
        995                    1000                   1005
Ile Asp Met Ala Gln Glu Ile Glu Lys Arg Asn Leu Gln Thr Arg Leu
    1010                   1015                   1020
Leu Leu Gln Val His Asp Glu Leu Val Phe Glu Ala Pro Lys Asp Glu
1025                   1030                   1035                   1040
Ile Glu Ile Leu Glu Lys Leu Val Pro Glu Val Met Glu Asn Ala Ile
                1045                   1050                   1055
Gln Leu Lys Val Pro Leu Lys Val Asp Tyr Ser Tyr Gly Ser Thr Trp
            1060                   1065                   1070
Tyr Asp Ala Lys Ser Ser His His His His His His
            1075                   1080
```

( 2 ) INFORMATION FOR SEQ ID NO:7:

( i ) SEQUENCE CHARACTERISTICS:
        ( A ) LENGTH: 3831 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..3828

( x i ) SEQUENCE DESCRIPTION: SEQ ID NO:7:

```
ATG AAA ATC GAA GAA GGT AAA CTG GTA ATC TGG ATT AAC GGC GAT AAA    48
Met Lys Ile Glu Glu Gly Lys Leu Val Ile Trp Ile Asn Gly Asp Lys
1085                   1090                   1095                   1100

GGC TAT AAC GGT CTC GCT GAA GTC GGT AAG AAA TTC GAG AAA GAT ACC    96
Gly Tyr Asn Gly Leu Ala Glu Val Gly Lys Lys Phe Glu Lys Asp Thr
                1105                   1110                   1115

GGA ATT AAA GTC ACC GTT GAG CAT CCG GAT AAA CTG GAA GAG AAA TTC   144
Gly Ile Lys Val Thr Val Glu His Pro Asp Lys Leu Glu Glu Lys Phe
            1120                   1125                   1130

CCA CAG GTT GCG GCA ACT GGC GAT GGC CCT GAC ATT ATC TTC TGG GCA   192
Pro Gln Val Ala Ala Thr Gly Asp Gly Pro Asp Ile Ile Phe Trp Ala
        1135                   1140                   1145

CAC GAC CGC TTT GGT GGC TAC GCT CAA TCT GGC CTG TTG GCT GAA ATC   240
His Asp Arg Phe Gly Gly Tyr Ala Gln Ser Gly Leu Leu Ala Glu Ile
    1150                   1155                   1160

ACC CCG GAC AAA GCG TTC CAG GAC AAG CTG TAT CCG TTT ACC TGG GAT   288
Thr Pro Asp Lys Ala Phe Gln Asp Lys Leu Tyr Pro Phe Thr Trp Asp
1165                   1170                   1175                   1180

GCC GTA CGT TAC AAC GGC AAG CTG ATT GCT TAC CCG ATC GCT GTT GAA   336
Ala Val Arg Tyr Asn Gly Lys Leu Ile Ala Tyr Pro Ile Ala Val Glu
                1185                   1190                   1195

GCG TTA TCG CTG ATT TAT AAC AAA GAT CTG CTG CCG AAC CCG CCA AAA   384
Ala Leu Ser Leu Ile Tyr Asn Lys Asp Leu Leu Pro Asn Pro Pro Lys
                1200                   1205                   1210

ACC TGG GAA GAG ATC CCG GCG CTG GAT AAA GAA CTG AAA GCG AAA GGT   432
Thr Trp Glu Glu Ile Pro Ala Leu Asp Lys Glu Leu Lys Ala Lys Gly
            1215                   1220                   1225

AAG AGC GCG CTG ATG TTC AAC CTG CAA GAA CCG TAC TTC ACC TGG CCG   480
Lys Ser Ala Leu Met Phe Asn Leu Gln Glu Pro Tyr Phe Thr Trp Pro
        1230                   1235                   1240
```

```
CTG ATT GCT GCT GAC GGG GGT TAT GCG TTC AAG TAT GAA AAC GGC AAG     528
Leu Ile Ala Ala Asp Gly Gly Tyr Ala Phe Lys Tyr Glu Asn Gly Lys
1245                1250                1255                1260

TAC GAC ATT AAA GAC GTG GGC GTG GAT AAC GCT GGC GCG AAA GCG GGT     576
Tyr Asp Ile Lys Asp Val Gly Val Asp Asn Ala Gly Ala Lys Ala Gly
                1265                1270                1275

CTG ACC TTC CTG GTT GAC CTG ATT AAA AAC AAA CAC ATG AAT GCA GAC     624
Leu Thr Phe Leu Val Asp Leu Ile Lys Asn Lys His Met Asn Ala Asp
            1280                1285                1290

ACC GAT TAC TCC ATC GCA GAA GCT GCC TTT AAT AAA GGC GAA ACA GCG     672
Thr Asp Tyr Ser Ile Ala Glu Ala Ala Phe Asn Lys Gly Glu Thr Ala
        1295                1300                1305

ATG ACC ATC AAC GGC CCG TGG GCA TGG TCC AAC ATC GAC ACC AGC AAA     720
Met Thr Ile Asn Gly Pro Trp Ala Trp Ser Asn Ile Asp Thr Ser Lys
1310                1315                1320

GTG AAT TAT GGT GTA ACG GTA CTG CCG ACC TTC AAG GGT CAA CCA TCC     768
Val Asn Tyr Gly Val Thr Val Leu Pro Thr Phe Lys Gly Gln Pro Ser
1325                1330                1335                1340

AAA CCG TTC GTT GGC GTG CTG AGC GCA GGT ATT AAC GCC GCC AGT CCG     816
Lys Pro Phe Val Gly Val Leu Ser Ala Gly Ile Asn Ala Ala Ser Pro
                1345                1350                1355

AAC AAA GAG CTG GCA AAA GAG TTC CTC GAA AAC TAT CTG CTG ACT GAT     864
Asn Lys Glu Leu Ala Lys Glu Phe Leu Glu Asn Tyr Leu Leu Thr Asp
            1360                1365                1370

GAA GGT CTG GAA GCG GTT AAT AAA GAC AAA CCG CTG GGT GCC GTA GCG     912
Glu Gly Leu Glu Ala Val Asn Lys Asp Lys Pro Leu Gly Ala Val Ala
        1375                1380                1385

CTG AAG TCT TAC GAG GAA GAG TTG GCG AAA GAT CCA CGT ATT GCC GCC     960
Leu Lys Ser Tyr Glu Glu Glu Leu Ala Lys Asp Pro Arg Ile Ala Ala
1390                1395                1400

ACC ATG GAA AAC GCC CAG AAA GGT GAA ATC ATG CCG AAC ATC CCG CAG    1008
Thr Met Glu Asn Ala Gln Lys Gly Glu Ile Met Pro Asn Ile Pro Gln
1405                1410                1415                1420

ATG TCC GCT TTC TGG TAT GCC GTG CGT ACT GCG GTG ATC AAC GCC GCC    1056
Met Ser Ala Phe Trp Tyr Ala Val Arg Thr Ala Val Ile Asn Ala Ala
                1425                1430                1435

AGC GGT CGT CAG ACT GTC GAT GAA GCC CTG AAA GAC GCG CAG ACT AAT    1104
Ser Gly Arg Gln Thr Val Asp Glu Ala Leu Lys Asp Ala Gln Thr Asn
            1440                1445                1450

TCG AGC TCG AAC AAC AAC AAC AAT AAC AAT AAC AAC AAC CTC GGG ATC    1152
Ser Ser Ser Asn Asn Asn Asn Asn Asn Asn Asn Asn Asn Leu Gly Ile
        1455                1460                1465

GAG GGA AGG ATT TCA GAA TTC GGC GTG ACA AAG AAG CTA GTT TTA ATT    1200
Glu Gly Arg Ile Ser Glu Phe Gly Val Thr Lys Lys Leu Val Leu Ile
1470                1475                1480

GAT GGA AAC AGT ATT GCT TAC AGA GCG TTT TTC GCT TTG CCG CTT TTA    1248
Asp Gly Asn Ser Ile Ala Tyr Arg Ala Phe Phe Ala Leu Pro Leu Leu
1485                1490                1495                1500

AAT AAT GAT AAG GGG ATT TAT ACG AAT GCA ATT TAC GGC TTT ACA AAT    1296
Asn Asn Asp Lys Gly Ile Tyr Thr Asn Ala Ile Tyr Gly Phe Thr Asn
                1505                1510                1515

ATG CTG TTA AAA GTA CTG GAG GAA GAA AAA CCG ACA CAT ATT CTT GTT    1344
Met Leu Leu Lys Val Leu Glu Glu Glu Lys Pro Thr His Ile Leu Val
            1520                1525                1530

GCA TTT GAT GCA GGG AAA ACA ACG TTC CGG CAT AAA ACT TTT AAA GAA    1392
Ala Phe Asp Ala Gly Lys Thr Thr Phe Arg His Lys Thr Phe Lys Glu
        1535                1540                1545

TAT AAA GGA ACT CGG CAA AAA ACC CCG CCT GAA TTG TCG GAG CAG CTA    1440
Tyr Lys Gly Thr Arg Gln Lys Thr Pro Pro Glu Leu Ser Glu Gln Leu
1550                1555                1560
```

```
CCA TTT ATA CGG GAT TTG CTT GAT GCC TAC CAA ATT ACA ACA TAT GAA      1488
Pro Phe Ile Arg Asp Leu Leu Asp Ala Tyr Gln Ile Thr Thr Tyr Glu
1565                1570                1575                1580

CTC GAA AAT TAT GAG GCT GAT GAT ATT ATT GGA ACA GTT GCG AGA CAA      1536
Leu Glu Asn Tyr Glu Ala Asp Asp Ile Ile Gly Thr Val Ala Arg Gln
            1585                1590                1595

GCT GAG AAG CAA GAT TTT GAA GTG AAA ATT ATT TCC GGA GAT AAG GAT      1584
Ala Glu Lys Gln Asp Phe Glu Val Lys Ile Ile Ser Gly Asp Lys Asp
        1600                1605                1610

TTA ACA CAG CTG GCA ACT GAA AAA ACG ACC GTT TCC ATC ACG AAA AAA      1632
Leu Thr Gln Leu Ala Thr Glu Lys Thr Thr Val Ser Ile Thr Lys Lys
    1615                1620                1625

GGA ATT ACA GAT GTT GAA CCG CAC ACG CCT GAA TCG ATT CAA GAG AAG      1680
Gly Ile Thr Asp Val Glu Pro His Thr Pro Glu Ser Ile Gln Glu Lys
1630                1635                1640

TAT GGG CTA AGC CCG GCA CAA ATT ATT GAT TTG AAA GGA TTG ATG GGC      1728
Tyr Gly Leu Ser Pro Ala Gln Ile Ile Asp Leu Lys Gly Leu Met Gly
1645                1650                1655                1660

GAT CAA TCA GAT AAT ATC CCA GGT GTG CCC GGC GTT GGA GAG AAA ACC      1776
Asp Gln Ser Asp Asn Ile Pro Gly Val Pro Gly Val Gly Glu Lys Thr
            1665                1670                1675

GCG ATT AAA TTG CTG AAA CAG TTT GAG ACA GTC GAA AAT ATT TTA AAT      1824
Ala Ile Lys Leu Leu Lys Gln Phe Glu Thr Val Glu Asn Ile Leu Asn
        1680                1685                1690

TCG ATT GAA GAA GTA AAT GGA AAA AAA TTG AAG GAA AAC TTA CAA AAC      1872
Ser Ile Glu Glu Val Asn Gly Lys Lys Leu Lys Glu Asn Leu Gln Asn
    1695                1700                1705

TAT AAA GAG CAA GCA TTA ATG AGC AAA CAG CTT GCG ACA ATT CAT TGT      1920
Tyr Lys Glu Gln Ala Leu Met Ser Lys Gln Leu Ala Thr Ile His Cys
1710                1715                1720

GAA GCT CCT GTC GAA ATA AAA ATT CAA GAC CTT GAG TAT AAA GGC TAT      1968
Glu Ala Pro Val Glu Ile Lys Ile Gln Asp Leu Glu Tyr Lys Gly Tyr
1725                1730                1735                1740

GAC AAA GAA AAA GTA GTG AAA ATT TTT AAG GAA CTA GGC TTC CAA TCG      2016
Asp Lys Glu Lys Val Val Lys Ile Phe Lys Glu Leu Gly Phe Gln Ser
            1745                1750                1755

CTC CTA GAC AAA ATG GGA GAG CAT GAG AAT GAA GAA GCG GAT GAA ATG      2064
Leu Leu Asp Lys Met Gly Glu His Glu Asn Glu Glu Ala Asp Glu Met
        1760                1765                1770

CCG ACG ATT AAG TTC GAA AAA GTT GAA AAG CTG TCA GAC AAG GTT TTA      2112
Pro Thr Ile Lys Phe Glu Lys Val Glu Lys Leu Ser Asp Lys Val Leu
    1775                1780                1785

TCA GAG AAG GCA GCT CTT TTA GTG GAA ATC ATT GAT GAA AAT TAT CAT      2160
Ser Glu Lys Ala Ala Leu Leu Val Glu Ile Ile Asp Glu Asn Tyr His
1790                1795                1800

ACT GGA GAA ATC ATC GGG TTT TCT ATC GCA AAC GAA AAT GGA TGT TTT      2208
Thr Gly Glu Ile Ile Gly Phe Ser Ile Ala Asn Glu Asn Gly Cys Phe
1805                1810                1815                1820

TAT ATT CCA GCC GAA ATT GCG CTA CAT TCA AAA GAG TTC ATA GAA TGG      2256
Tyr Ile Pro Ala Glu Ile Ala Leu His Ser Lys Glu Phe Ile Glu Trp
            1825                1830                1835

GTG AAG GAT GAA ACA AAG CGG AAA GTG GTG TAT GAT GCG AAA AAA TCA      2304
Val Lys Asp Glu Thr Lys Arg Lys Val Val Tyr Asp Ala Lys Lys Ser
        1840                1845                1850

ATT GTG GCG CTG CGC TGG CGA AAC ATT GAT TTA GCA GGT ATT GAG TTT      2352
Ile Val Ala Leu Arg Trp Arg Asn Ile Asp Leu Ala Gly Ile Glu Phe
    1855                1860                1865

GAT GTT CTC ATT GCC TCA TAC ATT TTA AAT CCG TCT GAA TCG ATT GAC      2400
Asp Val Leu Ile Ala Ser Tyr Ile Leu Asn Pro Ser Glu Ser Ile Asp
1870                1875                1880
```

```
GAC ATA GCC GAG CTT GCC AAG ACA AAA AAT AAA CAT TTA GTT CAA AAG            2448
Asp Ile Ala Glu Leu Ala Lys Thr Lys Asn Lys His Leu Val Gln Lys
1885                1890                1895                1900

GAT GAA GTG ATT TAC GGA AAA GGC GCT AAA CGT CAT ATC CCT GAT GAA            2496
Asp Glu Val Ile Tyr Gly Lys Gly Ala Lys Arg His Ile Pro Asp Glu
                1905                1910                1915

GAC ATT TTA GGC GAA CAT CTT GCC AGA AAA GCG TTA GCC ATT TAT GAG            2544
Asp Ile Leu Gly Glu His Leu Ala Arg Lys Ala Leu Ala Ile Tyr Glu
            1920                1925                1930

CTG GAA GAA TTA TTA ATA CAA GAA TTA GAA GAA AAT GAA CAA TTT CAT            2592
Leu Glu Glu Leu Leu Ile Gln Glu Leu Glu Glu Asn Glu Gln Phe His
        1935                1940                1945

TTA TTC AGC GAA TTG GAG CTT CCG CTG TCA GCC ATT TTA TCT GAC ATG            2640
Leu Phe Ser Glu Leu Glu Leu Pro Leu Ser Ala Ile Leu Ser Asp Met
    1950                1955                1960

GAA ACA ACA GGA GTA AAG ATA GAC GTC AAC CGT CTG AAA GAA ATG GGA            2688
Glu Thr Thr Gly Val Lys Ile Asp Val Asn Arg Leu Lys Glu Met Gly
1965                1970                1975                1980

AAA GAG CTT GAT GAA CAG CTG AAG CAA TTA GAA AAG GAT ATT CAT CGT            2736
Lys Glu Leu Asp Glu Gln Leu Lys Gln Leu Glu Lys Asp Ile His Arg
                1985                1990                1995

CTA GCT GGA GTG TCA TTT AAC ATT AAT TCT CCG AAG CAG CTT GGG CCG            2784
Leu Ala Gly Val Ser Phe Asn Ile Asn Ser Pro Lys Gln Leu Gly Pro
            2000                2005                2010

ATT TTA TTT GAA AAG CTC AAT CTA CCG GTT TTG AAA AAG ACC AAA ACG            2832
Ile Leu Phe Glu Lys Leu Asn Leu Pro Val Leu Lys Lys Thr Lys Thr
        2015                2020                2025

GGG TAT TCG ACC TCT GCG GAC GTT TTA GAA AAA TTG AGA GGA CAG CAC            2880
Gly Tyr Ser Thr Ser Ala Asp Val Leu Glu Lys Leu Arg Gly Gln His
    2030                2035                2040

GAA ATT GTG GAG AAA ATT TTG CAT TAC CGG CAG CTC GGA AAG CTT CAA            2928
Glu Ile Val Glu Lys Ile Leu His Tyr Arg Gln Leu Gly Lys Leu Gln
2045                2050                2055                2060

TCG ACG TAT ATT GAA GGG CTG CTG AAG GTT GTC CAT CGT GAT ACG CAT            2976
Ser Thr Tyr Ile Glu Gly Leu Leu Lys Val Val His Arg Asp Thr His
                2065                2070                2075

AAA ATC CAC ACC CGA TTT AAT CAA GCA TTA ACG CAA ACC GGA AGA TTA            3024
Lys Ile His Thr Arg Phe Asn Gln Ala Leu Thr Gln Thr Gly Arg Leu
            2080                2085                2090

AGC TCC ACA GAC CCG AAT TTG CAA AAC ATT CCG ATT CGC CTT GAG GAA            3072
Ser Ser Thr Asp Pro Asn Leu Gln Asn Ile Pro Ile Arg Leu Glu Glu
        2095                2100                2105

GGC CGC AAA ATT CGT CAA GCA TTT ATC CCT TCT GAA AAA GAT TGG GTC            3120
Gly Arg Lys Ile Arg Gln Ala Phe Ile Pro Ser Glu Lys Asp Trp Val
    2110                2115                2120

ATT TTT GCA GCG GAC TAT TCC CAG ATT GAA CTG CGA GTG CTT GCG CAT            3168
Ile Phe Ala Ala Asp Tyr Ser Gln Ile Glu Leu Arg Val Leu Ala His
2125                2130                2135                2140

ATA TCT GGA GAT GAA AAA TTG ATT GAA GCG TTT AAA CAA GAT CTT GAT            3216
Ile Ser Gly Asp Glu Lys Leu Ile Glu Ala Phe Lys Gln Asp Leu Asp
                2145                2150                2155

ATT CAT ACA AAA ACG GCG ATC GAT GTG TTC CAT GTC GAA GAA GAT AAA            3264
Ile His Thr Lys Thr Ala Ile Asp Val Phe His Val Glu Glu Asp Lys
            2160                2165                2170

GTG ACC TCC AAC ATG AGA AGA CAG GCA AAA GCA GTT AAT TTC GGG ATT            3312
Val Thr Ser Asn Met Arg Arg Gln Ala Lys Ala Val Asn Phe Gly Ile
        2175                2180                2185

GTT TAC GGA ATC AGC GAT TAC GGA TTG TCG CAA AAC TTA GGA ATT ACC            3360
Val Tyr Gly Ile Ser Asp Tyr Gly Leu Ser Gln Asn Leu Gly Ile Thr
    2190                2195                2200
```

```
CGA AAA GAA GCT GGT GAA TTT ATT AAA AAA TAT TTT GAA ATT TAT AAA      3408
Arg Lys Glu Ala Gly Glu Phe Ile Lys Lys Tyr Phe Glu Ile Tyr Lys
2205              2210                2215                2220

GGC GTT AAA GAA TAT ATG GAT GGC ATA ATC CAA GAG GCG AAG CAA AAA      3456
Gly Val Lys Glu Tyr Met Asp Gly Ile Ile Gln Glu Ala Lys Gln Lys
                  2225                2230                2235

GGC TAT GTA ACG ACA CTA ATG CAG CGT CGG AGA TAT ATT CCG GAA ATT      3504
Gly Tyr Val Thr Thr Leu Met Gln Arg Arg Arg Tyr Ile Pro Glu Ile
              2240                2245                2250

ACG AGC AGA AAT TTC AAT ATC AGA AGC TTC GCT GAG CGA ACA GCC ATG      3552
Thr Ser Arg Asn Phe Asn Ile Arg Ser Phe Ala Glu Arg Thr Ala Met
              2255                2260                2265

AAT ACT CCG ATT CAA GGA AGT GCA GCG GAT ATT ATC AAA AAA GCG ATG      3600
Asn Thr Pro Ile Gln Gly Ser Ala Ala Asp Ile Ile Lys Lys Ala Met
2270                2275                2280

ATC GAT ATG GCG CAA GAA ATT GAA AAA CGA AAT TTG CAA ACG AGG CTG      3648
Ile Asp Met Ala Gln Glu Ile Glu Lys Arg Asn Leu Gln Thr Arg Leu
2285                2290                2295                2300

CTG CTT CAA GTT CAT GAC GAA TTG GTG TTT GAA GCG CCA AAG GAT GAA      3696
Leu Leu Gln Val His Asp Glu Leu Val Phe Glu Ala Pro Lys Asp Glu
                  2305                2310                2315

ATT GAA ATT TTA GAA AAG CTT GTT CCG GAA GTA ATG GAA AAT GCC ATT      3744
Ile Glu Ile Leu Glu Lys Leu Val Pro Glu Val Met Glu Asn Ala Ile
              2320                2325                2330

CAG CTA AAA GTA CCG TTA AAG GTT GAT TAT TCT TAC GGT TCT ACG TGG      3792
Gln Leu Lys Val Pro Leu Lys Val Asp Tyr Ser Tyr Gly Ser Thr Trp
              2335                2340                2345

TAT GAC GCC AAA TCA TCT CAT CAT CAT CAT CAT CAT TAA                  3831
Tyr Asp Ala Lys Ser Ser His His His His His His
2350                2355                2360
```

( 2 ) INFORMATION FOR SEQ ID NO:8:

( i ) SEQUENCE CHARACTERISTICS:
        ( A ) LENGTH: 1276 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Lys Ile Glu Glu Gly Lys Leu Val Ile Trp Ile Asn Gly Asp Lys
 1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
 65                 70                  75                  80

Thr Pro Asp Lys Ala Phe Gln Asp Lys Leu Tyr Pro Phe Thr Trp Asp
                    85                  90                  95

Ala Val Arg Tyr Asn Gly Lys Leu Ile Ala Tyr Pro Ile Ala Val Glu
               100                 105                 110

Ala Leu Ser Leu Ile Tyr Asn Lys Asp Leu Leu Pro Asn Pro Pro Lys
           115                 120                 125

Thr Trp Glu Glu Ile Pro Ala Leu Asp Lys Glu Leu Lys Ala Lys Gly
       130                 135                 140
```

```
Lys  Ser  Ala  Leu  Met  Phe  Asn  Leu  Gln  Glu  Pro  Tyr  Phe  Thr  Trp  Pro
145                 150                      155                      160

Leu  Ile  Ala  Ala  Asp  Gly  Gly  Tyr  Ala  Phe  Lys  Tyr  Glu  Asn  Gly  Lys
                    165                      170                      175

Tyr  Asp  Ile  Lys  Asp  Val  Gly  Val  Asp  Asn  Ala  Gly  Ala  Lys  Ala  Gly
               180                      185                      190

Leu  Thr  Phe  Leu  Val  Asp  Leu  Ile  Lys  Asn  Lys  His  Met  Asn  Ala  Asp
          195                      200                    205

Thr  Asp  Tyr  Ser  Ile  Ala  Glu  Ala  Ala  Phe  Asn  Lys  Gly  Glu  Thr  Ala
     210                      215                    220

Met  Thr  Ile  Asn  Gly  Pro  Trp  Ala  Trp  Ser  Asn  Ile  Asp  Thr  Ser  Lys
225                 230                      235                      240

Val  Asn  Tyr  Gly  Val  Thr  Val  Leu  Pro  Thr  Phe  Lys  Gly  Gln  Pro  Ser
               245                      250                      255

Lys  Pro  Phe  Val  Gly  Val  Leu  Ser  Ala  Gly  Ile  Asn  Ala  Ala  Ser  Pro
               260                      265                      270

Asn  Lys  Glu  Leu  Ala  Lys  Glu  Phe  Leu  Glu  Asn  Tyr  Leu  Leu  Thr  Asp
          275                      280                      285

Glu  Gly  Leu  Glu  Ala  Val  Asn  Lys  Asp  Lys  Pro  Leu  Gly  Ala  Val  Ala
290                      295                      300

Leu  Lys  Ser  Tyr  Glu  Glu  Glu  Leu  Ala  Lys  Asp  Pro  Arg  Ile  Ala  Ala
305                      310                      315                      320

Thr  Met  Glu  Asn  Ala  Gln  Lys  Gly  Glu  Ile  Met  Pro  Asn  Ile  Pro  Gln
                    325                      330                      335

Met  Ser  Ala  Phe  Trp  Tyr  Ala  Val  Arg  Thr  Ala  Val  Ile  Asn  Ala  Ala
               340                      345                      350

Ser  Gly  Arg  Gln  Thr  Val  Asp  Glu  Ala  Leu  Lys  Asp  Ala  Gln  Thr  Asn
          355                      360                      365

Ser  Ser  Ser  Asn  Asn  Asn  Asn  Asn  Asn  Asn  Asn  Asn  Asn  Leu  Gly  Ile
          370                      375                      380

Glu  Gly  Arg  Ile  Ser  Glu  Phe  Gly  Val  Thr  Lys  Lys  Leu  Val  Leu  Ile
385                      390                      395                      400

Asp  Gly  Asn  Ser  Ile  Ala  Tyr  Arg  Ala  Phe  Phe  Ala  Leu  Pro  Leu  Leu
                    405                      410                      415

Asn  Asn  Asp  Lys  Gly  Ile  Tyr  Thr  Asn  Ala  Ile  Tyr  Gly  Phe  Thr  Asn
               420                      425                      430

Met  Leu  Leu  Lys  Val  Leu  Glu  Glu  Glu  Lys  Pro  Thr  His  Ile  Leu  Val
          435                      440                      445

Ala  Phe  Asp  Ala  Gly  Lys  Thr  Thr  Phe  Arg  His  Lys  Thr  Phe  Lys  Glu
     450                      455                      460

Tyr  Lys  Gly  Thr  Arg  Gln  Lys  Thr  Pro  Pro  Glu  Leu  Ser  Glu  Gln  Leu
465                      470                      475                      480

Pro  Phe  Ile  Arg  Asp  Leu  Leu  Asp  Ala  Tyr  Gln  Ile  Thr  Thr  Tyr  Glu
               485                      490                      495

Leu  Glu  Asn  Tyr  Glu  Ala  Asp  Asp  Ile  Ile  Gly  Thr  Val  Ala  Arg  Gln
               500                      505                      510

Ala  Glu  Lys  Gln  Asp  Phe  Glu  Val  Lys  Ile  Ile  Ser  Gly  Asp  Lys  Asp
          515                      520                      525

Leu  Thr  Gln  Leu  Ala  Thr  Glu  Lys  Thr  Thr  Val  Ser  Ile  Thr  Lys  Lys
     530                      535                      540

Gly  Ile  Thr  Asp  Val  Glu  Pro  His  Thr  Pro  Glu  Ser  Ile  Gln  Glu  Lys
545                      550                      555                      560

Tyr  Gly  Leu  Ser  Pro  Ala  Gln  Ile  Ile  Asp  Leu  Lys  Gly  Leu  Met  Gly
                    565                      570                      575
```

-continued

| | | | | | | | | | | | | | |
|---|---|---|---|---|---|---|---|---|---|---|---|---|---|
|Asp|Gln|Ser|Asp 580|Asn|Ile|Pro|Gly|Val 585|Pro|Gly|Val|Gly 590|Glu|Lys|Thr|
|Ala|Ile|Lys 595|Leu|Leu|Lys|Gln|Phe 600|Glu|Thr|Val|Glu|Asn 605|Ile|Leu|Asn|
|Ser|Ile 610|Glu|Glu|Val|Asn|Gly 615|Lys|Lys|Leu|Lys|Glu 620|Asn|Leu|Gln|Asn|
|Tyr 625|Lys|Glu|Gln|Ala|Leu 630|Met|Ser|Lys|Gln|Leu 635|Ala|Thr|Ile|His|Cys 640|
|Glu|Ala|Pro|Val|Glu 645|Ile|Lys|Ile|Gln|Asp 650|Leu|Glu|Tyr|Lys|Gly 655|Tyr|
|Asp|Lys|Glu|Lys 660|Val|Val|Lys|Ile|Phe 665|Lys|Glu|Leu|Gly|Phe 670|Gln|Ser|
|Leu|Leu|Asp 675|Lys|Met|Gly|Glu|His 680|Glu|Asn|Glu|Glu|Ala 685|Asp|Glu|Met|
|Pro|Thr 690|Ile|Lys|Phe|Glu|Lys 695|Val|Glu|Lys|Leu|Ser 700|Asp|Lys|Val|Leu|
|Ser 705|Glu|Lys|Ala|Ala|Leu 710|Leu|Val|Glu|Ile|Ile 715|Asp|Glu|Asn|Tyr|His 720|
|Thr|Gly|Glu|Ile|Ile 725|Gly|Phe|Ser|Ile|Ala 730|Asn|Glu|Asn|Gly|Cys 735|Phe|
|Tyr|Ile|Pro|Ala 740|Glu|Ile|Ala|Leu|His 745|Ser|Lys|Glu|Phe|Ile 750|Glu|Trp|
|Val|Lys|Asp 755|Glu|Thr|Lys|Arg|Lys 760|Val|Val|Tyr|Asp|Ala 765|Lys|Lys|Ser|
|Ile|Val 770|Ala|Leu|Arg|Trp|Arg 775|Asn|Ile|Asp|Leu|Ala 780|Gly|Ile|Glu|Phe|
|Asp 785|Val|Leu|Ile|Ala|Ser 790|Tyr|Ile|Leu|Asn|Pro 795|Ser|Glu|Ser|Ile|Asp 800|
|Asp|Ile|Ala|Glu|Leu 805|Ala|Lys|Thr|Lys|Asn 810|Lys|His|Leu|Val|Gln 815|Lys|
|Asp|Glu|Val|Ile 820|Tyr|Gly|Lys|Gly|Ala 825|Lys|Arg|His|Ile|Pro 830|Asp|Glu|
|Asp|Ile|Leu 835|Gly|Glu|His|Leu|Ala 840|Arg|Lys|Ala|Leu|Ala 845|Ile|Tyr|Glu|
|Leu|Glu 850|Glu|Leu|Leu|Ile|Gln 855|Glu|Leu|Glu|Glu|Asn 860|Glu|Gln|Phe|His|
|Leu 865|Phe|Ser|Glu|Leu|Glu 870|Leu|Pro|Leu|Ser|Ala 875|Ile|Leu|Ser|Asp|Met 880|
|Glu|Thr|Thr|Gly|Val 885|Lys|Ile|Asp|Val|Asn 890|Arg|Leu|Lys|Glu|Met 895|Gly|
|Lys|Glu|Leu|Asp 900|Glu|Gln|Leu|Lys|Gln 905|Leu|Glu|Lys|Asp|Ile 910|His|Arg|
|Leu|Ala|Gly 915|Val|Ser|Phe|Asn|Ile 920|Asn|Ser|Pro|Lys|Gln 925|Leu|Gly|Pro|
|Ile|Leu|Phe 930|Glu|Lys|Leu|Asn|Leu 935|Pro|Val|Leu|Lys|Lys 940|Thr|Lys|Thr|
|Gly 945|Tyr|Ser|Thr|Ser|Ala 950|Asp|Val|Leu|Glu|Lys 955|Leu|Arg|Gly|Gln|His 960|
|Glu|Ile|Val|Glu|Lys 965|Ile|Leu|His|Tyr|Arg 970|Gln|Leu|Gly|Lys|Leu 975|Gln|
|Ser|Thr|Tyr|Ile 980|Glu|Gly|Leu|Leu|Lys 985|Val|Val|His|Arg|Asp 990|Thr|His|
|Lys|Ile|His|Thr|Arg|Phe|Asn|Gln|Ala|Leu|Thr|Gln|Thr|Gly|Arg|Leu|

```
            995                        1000                       1005
Ser  Ser  Thr  Asp  Pro  Asn  Leu  Gln  Asn  Ile  Pro  Ile  Arg  Leu  Glu  Glu
     1010                     1015                    1020

Gly  Arg  Lys  Ile  Arg  Gln  Ala  Phe  Ile  Pro  Ser  Glu  Lys  Asp  Trp  Val
1025                1030                    1035                          1040

Ile  Phe  Ala  Ala  Asp  Tyr  Ser  Gln  Ile  Glu  Leu  Arg  Val  Leu  Ala  His
               1045                     1050                         1055

Ile  Ser  Gly  Asp  Glu  Lys  Leu  Ile  Glu  Ala  Phe  Lys  Gln  Asp  Leu  Asp
               1060                     1065                    1070

Ile  His  Thr  Lys  Thr  Ala  Ile  Asp  Val  Phe  His  Val  Glu  Glu  Asp  Lys
          1075                     1080                    1085

Val  Thr  Ser  Asn  Met  Arg  Arg  Gln  Ala  Lys  Ala  Val  Asn  Phe  Gly  Ile
     1090                     1095                    1100

Val  Tyr  Gly  Ile  Ser  Asp  Tyr  Gly  Leu  Ser  Gln  Asn  Leu  Gly  Ile  Thr
1105                     1110                    1115                     1120

Arg  Lys  Glu  Ala  Gly  Glu  Phe  Ile  Lys  Lys  Tyr  Phe  Glu  Ile  Tyr  Lys
                    1125                    1130                    1135

Gly  Val  Lys  Glu  Tyr  Met  Asp  Gly  Ile  Ile  Gln  Glu  Ala  Lys  Gln  Lys
               1140                     1145                    1150

Gly  Tyr  Val  Thr  Thr  Leu  Met  Gln  Arg  Arg  Arg  Tyr  Ile  Pro  Glu  Ile
          1155                     1160                    1165

Thr  Ser  Arg  Asn  Phe  Asn  Ile  Arg  Ser  Phe  Ala  Glu  Arg  Thr  Ala  Met
     1170                     1175                    1180

Asn  Thr  Pro  Ile  Gln  Gly  Ser  Ala  Ala  Asp  Ile  Ile  Lys  Lys  Ala  Met
1185                     1190                    1195                     1200

Ile  Asp  Met  Ala  Gln  Glu  Ile  Glu  Lys  Arg  Asn  Leu  Gln  Thr  Arg  Leu
               1205                     1210                    1215

Leu  Leu  Gln  Val  His  Asp  Glu  Leu  Val  Phe  Glu  Ala  Pro  Lys  Asp  Glu
               1220                     1225                    1230

Ile  Glu  Ile  Leu  Glu  Lys  Leu  Val  Pro  Glu  Val  Met  Glu  Asn  Ala  Ile
          1235                     1240                    1245

Gln  Leu  Lys  Val  Pro  Leu  Lys  Val  Asp  Tyr  Ser  Tyr  Gly  Ser  Thr  Trp
1250                     1255                    1260

Tyr  Asp  Ala  Lys  Ser  Ser  His  His  His  His  His  His
1265                     1270                    1275
```

THERMOSTABLE DNA POLYMERASE FROM *BACILLUS PALLIDUS*

FIELD OF THE INVENTION

The invention relates to DNA polymerases, genes coding for DNA polymerases and production of recombinant DNA polymerases.

BACKGROUND OF THE INVENTION

Type I DNA polymerases (Pol I) are ubiquitous enzymes in Eubacteria. They are multifunctional/multidomain enzymes which appear to be involved in DNA repair and DNA replication. The *E. coli* Pol I, and most other Type I DNA polymerases characterized to date, have three enzymatic activities: DNA polymerization (5'-3'), 3'-5' exonuclease activity and 5'-3' exonuclease activity. Each of these activities has been localized to a particular region or domain of the protein. In *E. coli* Pol I, the N-terminal domain (amino acids 1–324) encodes the 5'-3' exonuclease activity, the central domain (amino acids 324–517) encodes the 3'-5' exonuclease activity and the C-terminal domain (amino acids 521–928) encodes the DNA polymerase activity. When *E. coli* Pol I is cleaved into two fragments by subtilisin digestion, the larger fragment (Klenow fragment) has 3'-5' exonuclease and DNA polymerase activities and the smaller fragment has 5'-3' exonuclease activity.

DNA polymerase I has been isolated, cloned and sequenced from several eubacterial species, including *Streptococcus pneumoniae* (A. Diaz, et al. 1992. J. Bacteriol. 174:2014–2024), *Bacillus stearothermophilus* (S-M. Phang, et al. 1995. Gene 163:65–68 and WO 95/27067), *Bacillus caldotenax* (T. Uemori, et al. 1993. J. Biochem. 113:401–410), and *Thermus aquaticus* (Lawyer et al. 1993. PCR Methods and Applications. 2:275–287). The temperature optimum for activity of the *E. coli* and *S. pneumoniae* Pol I enzymes is about 37° C., i.e., they are mesophilic. In contrast, the polymerases of bacteria with higher temperature tolerance have higher temperature optima—about 60°–70° C. for the Bacillus species and about 80° C. for *T. aquaticus*. These polymerases are thermophilic and may be useful at the temperatures of PCR and thermophilic SDA.

Alignment of the amino acid sequences of DNA polymerase I from eubacterial and bacteriophage sources has shown conserved motifs in both the 5'-3' exonuclease domain and the DNA polymerase domain. These conserved sequences typically represent amino acids which are important for the structure and/or function of the enzyme. Based on knowledge of conserved sequences, "Klenow-like" forms of the polymerases of species other than *E. coli* (i.e., forms lacking the 5'-3' exonuclease activity) have also been reported. Absence of 5=-3' exonuclease activity is particularly important for use of the polymerases in Strand Displacement Amplification (SDA - G. T. Walker, et al. 1992. *Proc. Natl. Acad. Sci. USA* 89, 392–396; G. T. Walker, et al. 1992. *Nuc. Acids. Res.* 20, 1691–1696; U.S. Pat. No. 5,455, 166; U.S. Pat. No. 5,270,184; EP 0 684 315), as the SDA polymerase must lack 5'-3' exonuclease activity, either naturally or by genetic manipulation, to prevent digestion of the strand downstream of the nick. For SDA, the polymerase must also incorporate the derivatized deoxynucleoside triphosphates (dNTPs) required for amplification (nucleotide analogs such as αthio-dNTPs) and displace a downsteam single strand from a double stranded molecule starting at a single stranded nick. It is also desirable, but not required, that the polymerase be capable of incorporating dUTP to allow amplicon decontamination.

SUMMARY OF THE INVENTION

A novel DNA polymerase I has been identified in *Bacillus pallidus* (Bpa Pol I) and the gene encoding this Pol I has been cloned, sequenced and expressed to produce the polymerase. The full-length wild-type enzyme has thermophilic DNA polymerase activity and thermophilic 5'-3' exonuclease activity. A Klenow-like deletion which inactivates the 5'-3' exonuclease activity has been constructed and expressed to produce a polymerase which is particularly useful in SDA.

DETAILED DESCRIPTION OF THE INVENTION

Initially, the "Klenow-like" fragment of Bpa Pol I was cloned using multiple sequence alignments of DNA Pol I genes of other species available in the GenBank sequence database to design degenerate PCR primers based on relatively conserved sequences within the 5'-3' exonuclease domain and at the C-terminal end of the polymerase gene. The primers were designed to include restriction enzyme recognition sites which allowed cloning and expression of amplification products in the pBLUESCRIPT plasmid (Stratagene). The forward primer was designed based on alignment of the *B. caldotenax, B. stearothermophilus, E. coli* and *S. pneumoniae* Pol I genes. The reverse primer was designed based on alignment of the *B. caldotenax, B. stearothermophilus* and *S pneumoniae* Poi I genes. Two gene sequences for *B. stearothermophilus* were listed in GenBank, and both were used in the sequence alignments.

The degenerate PCR primers were as follows:

SEQ ID NO:1
TGCCAA<u>TCTAGA</u>AGGCGTGCCSGGCRTCGGKRAAAARAC
(XbaI site for cloning is underlined)

SEQ ID NO:2
CACCAA<u>GGATCC</u>SYTTTTATTTSGCGTCRTACCAYGT
(BamHI site for cloning is underlined)

*Bacillus pallidus* (ATCC#51176) was grown in the ATCC recommended culture medium at 55° C. and the genomic DNA was isolated using conventional techniques. Using the degenerate primers SEQ ID NO: 1 and SEQ ID NO:2, a 2 Kb segment of the genome was amplified. This segment was cloned in the pBLUESCRIPT vector and transformed into *E. coli*. The gene product was expressed in the transformants by induction with IPTG as recommended by the manufacturer of the cloning vector. Cell-free lysates were prepared and assayed for polymerase activity by incorporation of $^{32}$P-labeled nucleotides into activated calf thymus DNA (Pharmacia), as follows. The polymerase was serially diluted at room temperature in fleshly prepared enzyme diluent (25 mM K$_3$PO$_4$, pH 7.5, 50 mM ammonium sulfate, 10 mM 2-mercaptoethanol, 1 mg/ml BSA) and mixed on a vortex mixer. Ninety μL of reaction buffer (25 mM K$_3$PO$_4$ pH 7.5, 0.15 mM each dNTP, 4 mM MgCl$_2$, 4.5 μg/reaction activated calf thymus DNA, 0.3 mg/reaction activated calf thymus DNA, 0.3 ILL per reaction 3000 mCu/mmol α$^{32}$-P-dCTP) was added to each reaction tube and prewarmed for 5 minutes at the selected reaction temperature. After prewarming, 10 μL of the polymerase dilution was added and mixed on a vortex mixer. Blank reactions had only 10 μL of the enzyme diluent added. The reactions were incubated for 15 minutes at the selected reaction temperature, removing 15 μL aliquots at 2, 5, 10 and 15 minutes and adding them to 45 μL of 25 mM EDTA to stop the reaction. Similar time points were taken from the blank control. After all time points were taken, 40 ILL of the terminated reaction was spotted onto a DE-81 filter disk (representing 10 ILL of the original reaction). The filters were washed at least four times in 0.3M ammonium formate pH 8.0 (5 minutes each wash) using 10 mL per filter. Washing was performed by dropping the spotted filter into a beaker of ammonium formate and agitating gently every 2–3 minutes The waste was decanted and additional aliquots of the wash buffer were poured onto the filters. Following the last wash the filters were rinsed in methanol and placed on Whatman paper to dry for about 5 minutes. The filters were then placed in scintillation vials and counted. An increase in radioactivity retained by the filter indicated that the recombinant expression product of the transformant exhibited polymerase activity. Polymerase activity, wherein One unit (U) is defined as the amount required to incorporate 10 nmole of total nucleotide into acid insoluble form in 30 min., was calculated according to the following equation:

$$U/mL = (\text{net cpm}) (\text{nmole/cpm}) (1 \text{ u}/10 \text{ nmole}) (100\% \text{ dNTP}/\times \%\text{dXTP}) (1/0.01 \text{ mL enz added}) (\text{dilution factor})$$

wherein net cpm=total cpm incorporated at 30 min. point for total reaction, e.g., for the 100 µL reactions described above after 30 min., net cpm=(time point cpm) (10 µL counted) (30 min./10 min. time point)

nmole/cpm=specific activity of reaction

100% dNTP/×% dXTP=the ratio of total nucleotides to %G or C, or the ratio of total nucleotides to %A or T in the template DNA. Calf thymus DNA is about 22% G or C and 28% A or T. The value selected corresponds to the $^{32}$-P labeled nucleotide employed.

Specific activity of the reaction was typically determined by spotting 5 µL of the blank reaction (90 µL buffer mix+10 µL enzyme diluent) onto each of three DE-81 filters, counting the filters and obtaining the average cpm. Specific activity was calculated as (5 µL)(0.15 nmoles)/average cpm=nmole/cpm.

For example, the unit activity of a thermophilic polymerase was calculated as follows. The polymerase was assayed as described above using 10 µL of a 1:5000 dilution and 10 µL of a 1:10,000 dilution and $\alpha^{32}$P-dATP. Three time points were taken (5 minutes, 10 minutes and 15 minutes) and background counts on the filters as well as blank control reactions were included. The average background count on three filters was 1442 cpm. The average cpm of the blank control (2 ILL spotted on each of two filters) was 240,536 cpm, resulting in a specific activity of $1.24 \times 10^{-6}$ nmole/cpm. Units/mL were calculated for each time point of each dilution. As an example, U/mL for the 5 minute time point of the 1:5000 dilution was calculated as follows: net cpm= (3714 cpm−1442 cpm)(10 µL)(30 min./5 min.)=134,820 net cpm; U/mL=134,820 net cpm $(1.24 \times 10^{-6}$ nm/cpm)(0.1 U/nm)(3.57)(100)(5000)=29,841. Units/mL for each time point were averaged for each dilution. The dilution averages were averaged to obtain a combined average U/mL. In this example, the combined average was 26,494 U/mL.

To simplify purification of the recombinant polymerase and to obtain higher expression levels, the amplified fragment was recloned into the pMAL-c plasmid (New England BioLabs) as recommended by the manufacturer. These constructs placed the large fragment of the Bpa polymerase under the control of the lac promoter of *E. coli*. Upon induction with IPTG, transformed host cells expressed a fusion product which contained the large fragment of Bpa Pol I fused to the maltose binding protein (MBP, the male gene product). The coding sequence for this clone (clone MBP/Bpa-192) is shown in SEQ ID NO:5, wherein nucleotides 1–3237 code for the MBP/Bpa fusion protein and nucleotides 3238–3255 code for a polyhistidine affinity purification tag. The MBP portion of the fusion protein allows purification of the expression product on amylose resin. The MBP/Bpa Pol I fusion protein had a molecular weight of about 117 Kd and was expressed as about 5–10% of total cell protein. The deduced amino acid sequence of the fusion protein is shown in SEQ ID NO:6, amino acids 1–1078.

The MBP/Bpa Pol I fusion protein was purified on amylose resin according to the protocol recommended by New England BioLabs. A temperature profile in the DNA polymerase activity assay showed activity between about 30° C. and about 75° C. with optimal activity at about 65° C. In a primer extension assay in which two adjacent primers were hybridized to a target sequence to stage a "nick", the polymerase was shown to be capable of initiating synthesis from a nick and displacing a downstream primer, indicating utility in SDA. Amplification was demonstrated in a thermophilic SDA reaction (EP 0 684 3 15), confirming strand displacing ability, the absence of 5'-3' exonuclease activity and an ability to incorporate dNTP analogs. The fewest number of initial targets tested for amplification (1,000) was detectable in the SDA reaction with 3 units of Bpa Pol I and 80 units of BsoBI. A unit of Bpa Pol I activity was defined in the $^{32}$P-incorporation assay described above and corresponds to the amount of polymerase which incorporates 10 nM of nucleotide in 30 min. Reverse transcriptase activity in the presence of $Mn^{2+}$ was demonstrated in an assay in which the polymerase extended a DNA primer annealed to an RNA template.

To isolate the full-length genomic copy of the Bpa Pol I gene, a genomic library or *B. pallidus* DNA was constructed by cloning genomic DNA digested with BclI into a λZAP vector (Stratagene). The library was screened by hybridization to the Bpa Pol I PCR product and a 5.8 Kb DNA fragment containing the Bpa Pol I gene was identified and isolated. The DNA sequence of this fragment was determined by conventional sequencing techniques and was found to contain the full-length coding sequence for Bpa Pol I as well as two open reading frames upstream from the Bpa Pol I gene and two open reading frames downstream from the Bpa Pol I gene. The coding sequence for the full-length Bpa Pol I is shown in SEQ 112) NO:3 and the deduced amino acid sequence of the full-length polymerase encoded by SEQ ID NO:3 is shown in SEQ ID NO:4. The large fragment initially cloned, in which the 5'-3' exonuclease domain is deleted, corresponds to amino acids 192–876 of SEQ ID NO:4 and is encoded by nucleotides 574–2628 of SEQ ID NO:3. Amino acid sequence comparison revealed 68% similarity to Bst polymerase (*B. stearothermophilus*, Riggs et al. 1995) and 67% similarity to Bca polymerase (*B. caldotenax*, Uemori et al. 1993). The full-length Bpa Pol I gene was cloned into pMAL-c to produce a MBP fusion protein. This clone was designated MBP/Bpa-1 and was shown to express thermophilic DNA polymerase activity and thermophilic 5'-3' exonuclease activity in the assays previously described. MBP/Bpa-1 expresses the nucleic acid sequence shown in SEQ ID NO:7 to produce Bpa Pol I having the amino acid sequence shown in SEQ ID NO:8. Nucleotides 1–3810 of SEQ ID NO:7 code for the MBP/Bpa fusion protein and nucleotides 3811–3828 code for a polyhistidine affinity purification tag. In SEQ ID NO:8, amino acids 1–1270 represent the MBP/Bpa fusion protein and amino acids 1271–1276 are the added polyhistidine affinity purification tag.

In addition, the large fragment with the 5'-3' exonuclease domain deleted was subcloned into plasmid pTRC99A (Pharmacia) without the MBP purification tag. This clone, designated pTRC/Bpal was deposited under the Budapest Treaty with the American Type Culture Collection, Rockville, Md., as ATCC Accession No. 98160 on Aug. 30, 1996. The large fragment may be derived from the deposited full-length clone using conventional methods for genetic manipulation such as in vitro mutagenesis and cloning. Expression of the polymerase in pTRC/Bpal produced an unfused polymerase protein which was tested in SDA as previously described. The polymerase supported amplification, confirming that the 5'-3' exo⁻ activity was inactive and that the unfused polymerase possessed the other activities required for SDA (strand displacing activity, initiation at a nick and incorporation of modified dNTPs).

When no affinity purification tag is present the polymerase protein may be purified, for example, as follows. $E.$ $coli$ cells expressing recombinant Bpa Pol I (about 1.28 g of cell paste) were isolated from the culture medium and resuspended in 3 mL of lysis buffer (20 mM imidazole-HCl pH 6.94, 0.2M KCl, 10% glycerol (w/v), 0.5 mM Na$_2$EDTA, 1 mM DTT) and the cell clumps were broken up using a pipette. The cell suspension was sonicated for 10 minutes in 20 second bursts to lyse the cells and centrifuged to remove cell debris. Of course, when a secretory expression system for the recombinant polymerase is employed lysis of the cells is not necessary. In these systems the cells are separated from the culture medium and the culture medium rather than a cell lysate is processed according to the following protocol to isolate the polymerase. The supernatant of the centrifuged cell lysate was then heated at 55° C. for 15 min. in a water bath and centrifuged 15 min. in a microcentrifuge to pellet the denatured proteins. Solid ammonium sulfate was added to the supernatant to 25% saturation. The sample was incubated with gentle agitation at 4° C. for 15 min. and microcentrifuged in the cold for 15 min. The supernatant was removed to a new microcentrfuge tube and lysis buffer saturated with ammonium sulfate was added to give the desired % saturation, followed by gentle agitation for 15 min. and centrifugation as before. The ammonium sulfate cuts taken were 35%, 45%, 55% and 65% saturation. The pellets of all ammonium sulfate cuts were quick-frozen in a dry ice-ethanol bath and stored at −76° C. while polymerase activity assays as described above were performed on samples taken from the lysis and fractionation steps to evaluate the efficiency of the purification process. The 65% ammonium sulfate saturated supernatant was stored on ice during the polymerase assays.

The polymerase activity present in the crude cell extract was stable through the heat treatment, with about 86% of total activity recovered and a 75% reduction in the total protein concentration as estimated by UV absorbance measurements. This corresponds to at least a 3-fold enrichment of the Bpa polymerase in a single simple step. Bpa Pol I appeared to be resistant to precipitation by ammonium sulfate. Most of the activity remained in the 65% saturated supernatant, although about 20% did precipitate and was recovered in the 55% and 65% pellets. Either method may therefore be employed at this step of the purification process, i.e., recovering the polymerase in the pellet at 55% ammonium sulfate or higher, or recovering the polymerase in the supernatant of about a 50–55% ammonium sulfate cut.

The pooled 65% ammonium sulfate supernatant and the resuspended 55% and 65% ammonium sulfate pellets were dialyzed for 4 hours against 750 volumes of Buffer A, diluted 5-fold in 20 mM imidazole-HCl pH 6.94, 20 mM KCl, 10% glycerol (w/v), 0.5 mM Na$_2$EDTA, 1 mM DTT (Buffer A) and loaded at a flow rate of 0.25 mL/min. onto a DEAE cellulose column equilibrated in Buffer A. After sample loading, Buffer A flow was continued at 0.25 mL/min. until UV monitoring of the fluid exiting the column indicated protein was present. At this point, collection of 1 mL fractions was begun and the flow rate was increased to 1 mL/min. The column was washed with Buffer A for 20 min. at this flow rate. A linear gradient (60 mL total gradient volume) from Buffer A to Buffer B (Buffer A+1M KCl) was initiated. At the end of the gradient, Buffer B was continued for 20 min., then a linear gradient of Buffer B to Buffer A was initiated (20 mL total gradient volume). At the end of the second gradient, the column was washed with Buffer A for 20 min. The collected fractions were stored at 4° C. until assayed for protein on 10% polyacrylamide, 0.1% SDS gels with 4% stacking gels and assayed for polymerase activity as described above.

Polymerase activity eluted at about 0.3M KCl, correlating with one of the absorbing peaks of the UV absorbance trace. There was about a two-fold concentration of activity when compared to the volume of sample loaded on the column. Photography of polyacrylamide gels stained with 30% methanol, 10% acetic acid, 0.05% Coomassie Brilliant Blue R-250 and destained in 30% methanol, 10% acetic acid showed that the protein was about 50% pure. The polymerase migrated slightly below the 68 kd marker, consistent with its predicted size.

The active fractions from the DEAE-cellulose column were pooled and dialyzed against KKEGD buffer (20 mM K$_2$PO$_4$ pH 7.4, 20 mM KCl, 10% glycerol (w/v), 1 mM DTT, 0.5 mM Na$_2$EDTA) for 4 hr. at 4° C. One mL of the dialyzed DEAE pool was diluted with 1 mL of KKEGD buffer and injected into a HITRAP Heparin column (Pharmacia) equilibrated with 20 mL of KKEGD buffer. Buffer flow was initiated at 0.25 mL/min. until UV absorbing material was detected in the eluate. The flow rate was then increased to 0.5 mL/min. and the column was washed for 10 min. with KKEGD buffer. A linear gradient from KKEGD to KKEGD, 1M KCl was initiated (10 mL total gradient volume) and 0.5 mL fractions were collected. At the end of the gradient the KKEGD, 1M KCl wash was continued for 10 min. and a linear gradient from KKEGD, 1M KCl to KKEGD was initiated (5 mL total gradient volume). At the end of the gradient the column was washed with KKEGD for 10 min.. The collected fractions were stored at 4° C. until assayed for protein and polymerase activity. The UV absorbance profile showed only a single peak.

Analysis on polyacrylamide gels indicated the polymerase was greater than 90% pure after heparin column chromatography. The fractions containing the highest levels of polymerase activity were pooled, concentrated and exchanged into KKEGD buffer by CENTRICON-30 ultrafiltration. The unit concentration of the purified stock was about 38,000 units/mL and the total protein concentration was about 0.6 mg/mL based on a Bradford assay. Yield was about 30 µg from one third of the DEAE active pool. The yield per gram of cells was therefore calculated to be about 70 µg, i.e., about 1 mg of protein per 14 g of cells. The estimated specific activity of this prep was 63,000 units/mg of protein.

It will be apparent from the foregoing description of the invention that several modifications are possible. First, the MBP affinity purification tag may be linked to either the N-terminus or the C-terminus of Bpa Pol I. Histidine residues (poly-histidine) added at the C-terminus or the N-terminus provide a heterologous amino acid sequence which is useful for purification of the polymerase by immobilized metal affinity chromatography (IMAC, e.g., nickel). The heterologous amino acids in the fusion protein do not adversely affect polymerase activity. Further, two heterologous sequences (e.g., two affinity purification tags) may be linked to the polymerase (one at each end), if desired, without significant adverse effects on polymerase activity. Additional alternative heterologous amino acid sequences are known in the art and may be linked to Bpa Pol I by conventional methods to produce various fusion proteins. Materials and methods for linking heterologous coding sequences such as affinity purification tags to the ends of the Bpa Pol I coding sequence and expression of the fusion proteins are well known in the art, as are methods for affinity purification of the fusion protein when the heterologous sequence is an affinity purification tag.

Further, due to degeneracy of the genetic code, different but equivalent nucleotide sequences which code for the Bpa Pol I enzyme of the invention (e.g., as shown in SEQ ID NO:4, amino acids 192–876 of SEQ ID NO:4, SEQ ID NO:6 or SEQ ID NO:8) may be isolated or prepared without the exercise of inventive skill. Such degenerate coding sequences are included within the scope of the invention. It is also within the ordinary skill in the art to clone DNA fragments encoding the Bpa Pol I of the invention into a variety of cloning vectors and to express the recombinant Bpa Pol I protein under the control of a promoter in a variety of transformed prokaryotic and eukaryotic host cells.

Extensive amino acid sequence analyses of prior art polymerase I enzymes have revealed highly conserved motifs. These motifs are known to correspond to regions of the protein required for the various activities. See, for example, L. Blanco, et al. 1991. Gene 100:27–38; M. Delarue, et al. 1990. Prot. Eng. 3:461–467; P. Gutman and K. Minton. 1993. Nucl. Acids Res. 21:4406–4407. By comparing the amino acid sequence of the Bpa Pol I of the invention to the teachings of these publications and others, it will be possible to identify the corresponding conserved motifs in the inventive polymerase. Amino acid substitutions in the regions of the protein outside the conserved motifs, particularly conservative amino acid substitutions, would be expected to have little if any effect on the biological activity of the polymerase. One skilled in the art would therefore expect that conservative (and certain non-conservative) amino acid substitutions in regions outside the conserved motifs would result in a Bpa Pol I variant which is substantially equivalent to the enzyme having the specific amino acid sequences herein disclosed. Such minor sequence variations are exemplified, but not limited to, the variant C-terminal sequences of SEQ ID NOs:6 and 8, where the amino acid sequence was altered in making the linkage to the histidine affinity purification tag. These variant Bpa Pol I polymerases and the nucleic acid sequences which encode them are considered to be substantial equivalents of the Bpa Pol I of the invention and are intended to be included within its scope.

What is claimed is:

1. An isolated nucleic acid sequence selected from the group consisting of nucleic acid sequences encoding SEQ ID NO:4, nucleic acid sequences encoding amino acids 192–876 of SEQ ID NO:4, SEQ ID NO:3, nucleotides 574–2628 of SEQ ID NO:3, SEQ ID NO:5, nucleotides 1–3237 of SEQ ID NO:5, nucleic acid sequences encoding amino acids 1–1078 of SEQ ID NO:6, SEQ ID NO:7, nucleotides 1–3810 of SEQ ID NO:7, and nucleic acid sequences encoding amino acids 1–1270 of SEQ ID NO:8.

2. A recombinant vector comprising a nucleic acid sequence according to claim 1.

3. The recombinant vector of claim 2 which is an expression vector.

4. The recombinant vector of claim 3 wherein the expression vector encodes a fusion protein.

5. The recombinant vector of claim 4 wherein the fusion protein comprises an affinity purification tag.

6. A host cell transformed with the recombinant vector of claim 2.

7. The transformed host cell of claim 6 which is an E. coli host cell.

8. A host cell transformed with the recombinant vector of claim 3.

9. The transformed host cell of claim 8 which is an E. coli host cell.

10. A method for producing a recombinant DNA polymerase comprising culturing the transformed host cell of claim 6 in a culture medium under conditions whereby the recombinant DNA polymerase is expressed by the transformed host cell.

11. The method of claim 10 wherein expression of the recombinant DNA polymerase is induced during culture.

12. The method of claim 10 further comprising purifying the expressed recombinant DNA polymerase from a cell lysate or the culture medium.

13. The method of claim 12 wherein the recombinant DNA polymerase is purified by means of an affinity purification tag.

14. The method of claim 12 wherein the recombinant DNA polymerase is purified by a method comprising:

a) heating the cell lysate or culture medium and separating heat-denatured proteins from the the cell lysate or culture medium to produce a first supernatant containing the DNA polymerase;

b) adding ammonium sulfate to the first supernatant in an amount sufficient to precipitate contaminating proteins and form a second supernatant containing the DNA polymerase, or adding ammonium sulfate to the first supernatant in an amount sufficient to form a precipitate containing the DNA polymerase while maintaining contaminating proteins in solution;

c) subjecting the second supernatant containing the DNA polymerase or the precipitate containing the DNA polymerase to anion exchange chromatography and collecting fractions containing the DNA polymerase;

d) chromatographing the fractions containing the DNA polymerase on a heparin affinity column and collecting fractions containing the purified DNA polymerase.

15. An isolated DNA polymerase having a sequence selected from the group consisting of SEQ ID NO:4, amino acids 192–876 of SEQ ID NO:4, fusion proteins comprising SEQ ID NO:4, and fusion proteins comprising amino acids 192–876 of SEQ ID NO:4.

16. The DNA polymerase of claim 15 wherein the fusion protein is SEQ ID NO:6 or SEQ ID NO:8.

17. A method of making a recombinant vector for expression of a DNA polymerase in a transformed host cell comprising cloning a nucleic acid sequence selected from the group consisting of SEQ ID NO:3, nucleotides 574–2628 of SEQ ID NO:3, nucleic acid sequences encoding SEQ ID NO:4 and nucleic acid sequences encoding amino acids 192–876 of SEQ ID NO:4 into an expression vector under control of a promoter such that the polymerase is expressible in the transformed host cell.

18. The method of claim 17 wherein the nucleic acid sequence is cloned under control of a lac promoter.

19. The method of claim 17 wherein the nucleic acid sequence is cloned such that expression of the polymerase produces a fusion protein.

20. The method of claim 19 wherein the fusion protein comprises an affinity purification tag.

21. The method of claim 20 wherein the affinity purification tag is maltose binding protein or polyhistidine.

* * * * *